US007217691B2

(12) United States Patent
Wang et al.

(10) Patent No.: US 7,217,691 B2
(45) Date of Patent: *May 15, 2007

(54) METHODS OF TREATMENT OF PERIODONTAL DISEASE

(75) Inventors: Elizabeth Wang, Carlisle, MA (US); John M. Wozney, Hudson, MA (US); Vicki A. Rosen, Brookline, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/397,214

(22) Filed: Mar. 27, 2003

(65) Prior Publication Data

US 2004/0009916 A1    Jan. 15, 2004
US 2005/0159348 A9    Jul. 21, 2005

Related U.S. Application Data

(60) Continuation of application No. 09/804,625, filed on Mar. 9, 2001, which is a continuation of application No. 08/925,779, filed on Sep. 9, 1997, now Pat. No. 6,245,889, which is a continuation of application No. 07/721,847, filed on Jun. 14, 1991, now Pat. No. 6,150,328, and a continuation-in-part of application No. 07/655,579, filed on Mar. 18, 1991, now Pat. No. 5,618,924, which is a continuation-in-part of application No. 07/493,272, filed on Mar. 14, 1990, now abandoned, said application No. 07/493,272 is a continuation-in-part of application No. 07/406,217, filed on Sep. 12, 1989, now abandoned, and a continuation-in-part of application No. 07/378,537, filed on Jul. 11, 1989, now Pat. No. 5,166,058, said application No. 07/655,579 is a division of application No. 07/179,100, filed on Apr. 8, 1988, now Pat. No. 5,013,649, said application No. 07/378,537 is a continuation-in-part of application No. 07/179,100.

(51) Int. Cl.
*A61K 38/18* (2006.01)
*A61K 38/39* (2006.01)
*C07K 14/51* (2006.01)

(52) U.S. Cl. .................. 514/12; 514/801; 514/900; 530/300; 530/350

(58) Field of Classification Search .................. 514/12, 514/801; 530/350, 300; 562/589; 424/486
See application file for complete search history.

(56) References Cited

U.S. PATENT DOCUMENTS

| 2,465,357 | A |   | 3/1949  | Correll et al. |
|-----------|---|---|---------|----------------|
| 3,955,719 | A |   | 5/1976  | Pheulpin       |
| 4,191,747 | A |   | 3/1980  | Scheicher      |
| 4,294,753 | A |   | 10/1981 | Urist ............... 530/395 |
| 4,394,370 | A | * | 7/1983  | Jefferies ............... 606/76 |
| 4,399,216 | A |   | 8/1983  | Axel et al.    |
| 4,419,446 | A |   | 12/1983 | Howley et al.  |
| 4,434,094 | A |   | 2/1984  | Seyedin et al. ............ 530/416 |
| 4,441,915 | A |   | 4/1984  | Arndt et al.   |
| 4,455,256 | A |   | 6/1984  | Urist ............... 530/350 |
| 4,468,464 | A |   | 8/1984  | Cohen et al.   |
| 4,472,840 | A |   | 9/1984  | Jefferies      |
| 4,553,542 | A |   | 11/1985 | Schenck et al. |
| 4,563,350 | A |   | 1/1986  | Nathan et al. ............ 424/95 |
| 4,596,574 | A |   | 6/1986  | Urist          |
| 4,608,199 | A |   | 8/1986  | Caplan et al. ............ 530/414 |
| 4,619,989 | A |   | 10/1986 | Urist ............... 530/417 |
| 4,627,982 | A |   | 12/1986 | Seyedin et al. ............ 424/95 |
| 4,642,120 | A |   | 2/1987  | Nevo et al.    |
| 4,662,884 | A |   | 5/1987  | Stensaas       |
| 4,681,763 | A |   | 7/1987  | Nathanson ............ 424/95 |
| 4,703,008 | A |   | 10/1987 | Lin            |
| 4,727,028 | A |   | 2/1988  | Santerre et al. |
| 4,737,578 | A |   | 4/1988  | Evans ............... 530/350 |
| 4,758,233 | A |   | 7/1988  | Phillips et al. |
| 4,761,471 | A |   | 8/1988  | Urist ............... 530/350 |
| 4,766,067 | A |   | 8/1988  | Biswas et al.  |
| 4,767,628 | A |   | 8/1988  | Hutchinson     |
| 4,769,328 | A |   | 9/1988  | Murray et al.  |
| 4,774,228 | A |   | 9/1988  | Seyedin ............ 514/21 |
| 4,774,322 | A |   | 9/1988  | Seyedin ............ 530/353 |
| 4,784,055 | A |   | 11/1988 | Langen et al.  |
| 4,789,732 | A |   | 12/1988 | Urist ............... 530/350 |
| 4,795,804 | A |   | 1/1989  | Urist ............... 530/350 |
| 4,798,885 | A |   | 1/1989  | Mason ............... 530/350 |
| 4,804,744 | A |   | 2/1989  | Sen ............... 530/350 |
| 4,810,691 | A |   | 3/1989  | Seyedin ............ 514/2 |
| 4,828,990 | A |   | 5/1989  | Higashi et al. |
| 4,843,063 | A |   | 6/1989  | Seyedin ............ 514/2 |

(Continued)

FOREIGN PATENT DOCUMENTS

CA          2 017 466        5/1990

(Continued)

OTHER PUBLICATIONS

Urist et al., "Bone Cell Differentiation and Growth Factors," *Science*, 220: 680-686 (1983).

(Continued)

*Primary Examiner*—David Romeo
(74) *Attorney, Agent, or Firm*—Finnegan, Henderson, Farabow, Garrett & Dunner, LLP

(57) ABSTRACT

Purified BMP-2 and BMP-4 proteins and processes for producing them are disclosed. The proteins may be used in the treatment of bone and cartilage defects and in wound healing and related tissue repair.

8 Claims, 7 Drawing Sheets

U.S. PATENT DOCUMENTS

| | | | |
|---|---|---|---|
| 4,851,521 A | 7/1989 | Della Valle et al. | |
| 4,868,161 A | 9/1989 | Roberts | |
| 4,877,864 A * | 10/1989 | Wang et al. | 514/12 |
| 4,886,747 A | 12/1989 | Derynck | 435/69.5 |
| 4,908,204 A | 3/1990 | Robinson et al. | |
| 4,920,962 A | 5/1990 | Proulx | |
| 4,923,805 A | 5/1990 | Reddy et al. | |
| 4,955,892 A | 9/1990 | Daniloff et al. | |
| 4,963,146 A | 10/1990 | Li | |
| 4,968,590 A | 11/1990 | Kuberasampath et al. | 530/326 |
| 4,992,274 A | 2/1991 | Robinson et al. | |
| 5,011,486 A | 4/1991 | Aebischer et al. | |
| 5,011,691 A | 4/1991 | Oppermann | 424/423 |
| 5,013,649 A * | 5/1991 | Wang et al. | 435/69.1 |
| 5,019,087 A | 5/1991 | Nichols | |
| 5,024,841 A | 6/1991 | Chu et al. | |
| 5,026,381 A | 6/1991 | Li | |
| 5,041,538 A | 8/1991 | Ling et al. | |
| 5,071,834 A | 12/1991 | Burton et al. | |
| 5,089,396 A | 2/1992 | Mason et al. | |
| 5,102,807 A | 4/1992 | Burger et al. | |
| 5,106,626 A | 4/1992 | Parsons | 424/423 |
| 5,106,748 A | 4/1992 | Wozney et al. | |
| 5,108,753 A | 4/1992 | Kuberasampath | 424/422 |
| 5,108,922 A | 4/1992 | Wang et al. | |
| 5,116,738 A * | 5/1992 | Wang et al. | 435/69.1 |
| 5,118,667 A | 6/1992 | Adams et al. | |
| 5,124,316 A | 6/1992 | Antoniades et al. | |
| 5,141,905 A * | 8/1992 | Rosen et al. | 435/69.1 |
| 5,147,399 A | 9/1992 | Dellon et al. | |
| 5,166,058 A | 11/1992 | Wang et al. | |
| 5,166,190 A | 11/1992 | Mather et al. | |
| 5,166,322 A | 11/1992 | Shaw et al. | |
| 5,168,050 A | 12/1992 | Hammonds | 435/69.1 |
| 5,171,579 A | 12/1992 | Ron et al. | |
| 5,187,076 A * | 2/1993 | Wozney et al. | 435/69.1 |
| 5,187,263 A | 2/1993 | Murray et al. | |
| 5,202,120 A | 4/1993 | Silver et al. | |
| 5,206,028 A | 4/1993 | Li | |
| 5,208,219 A | 5/1993 | Ogawa et al. | |
| 5,215,893 A | 6/1993 | Mason et al. | |
| 5,216,126 A | 6/1993 | Cox et al. | |
| 5,217,867 A | 6/1993 | Evans et al. | |
| 5,218,090 A | 6/1993 | Connors | |
| 5,229,495 A | 7/1993 | Ichijo et al. | |
| 5,256,418 A | 10/1993 | Kemp et al. | |
| 5,258,494 A | 11/1993 | Oppermann et al. | |
| 5,266,683 A | 11/1993 | Oppermann et al. | |
| 5,278,145 A | 1/1994 | Keller et al. | |
| 5,284,756 A | 2/1994 | Grinna et al. | |
| 5,286,654 A | 2/1994 | Cox et al. | |
| 5,290,271 A | 3/1994 | Jernberg | |
| 5,292,802 A | 3/1994 | Rhee et al. | |
| 5,306,307 A | 4/1994 | Senter et al. | |
| 5,308,889 A | 5/1994 | Rhee et al. | |
| 5,324,519 A | 6/1994 | Dunn et al. | |
| 5,324,775 A | 6/1994 | Rhee et al. | |
| 5,328,955 A | 7/1994 | Rhee et al. | |
| 5,352,715 A | 10/1994 | McMullin et al. | |
| 5,354,557 A | 10/1994 | Oppermann et al. | |
| 5,356,629 A | 10/1994 | Sander et al. | |
| 5,364,839 A | 11/1994 | Gerhart et al. | |
| 5,366,875 A * | 11/1994 | Wozney et al. | 435/69.1 |
| 5,399,346 A | 3/1995 | Anderson et al. | |
| 5,399,677 A | 3/1995 | Wolfman et al. | |
| 5,405,390 A | 4/1995 | O'Leary et al. | |
| 5,411,941 A | 5/1995 | Grinna et al. | |
| 5,413,989 A | 5/1995 | Ogawa et al. | |
| 5,420,243 A | 5/1995 | Ogawa et al. | |
| 5,422,340 A | 6/1995 | Ammann et al. | |
| 5,447,725 A | 9/1995 | Damaini et al. | |
| 5,455,041 A | 10/1995 | Genco et al. | |
| 5,455,329 A | 10/1995 | Wingender | |
| 5,457,047 A | 10/1995 | Wingender | |
| 5,457,092 A | 10/1995 | Schluter | |
| 5,459,047 A | 10/1995 | Wozney et al. | |
| 5,464,440 A | 11/1995 | Johansson | |
| 5,508,263 A | 4/1996 | Grinna et al. | |
| 5,516,654 A | 5/1996 | Israel | |
| 5,520,923 A | 5/1996 | Tjia et al. | |
| 5,538,892 A | 7/1996 | Donahoe et al. | |
| 5,543,394 A * | 8/1996 | Wozney et al. | 514/12 |
| 5,545,616 A | 8/1996 | Woddruff | |
| 5,547,854 A | 8/1996 | Donahoe et al. | |
| 5,556,767 A | 9/1996 | Rosen et al. | |
| 5,618,924 A | 4/1997 | Wang et al. | |
| 5,631,142 A | 5/1997 | Wang et al. | |
| 5,635,372 A | 6/1997 | Celeste et al. | |
| 5,635,373 A | 6/1997 | Wozney et al. | |
| 5,637,480 A | 6/1997 | Celeste et al. | |
| 5,639,638 A | 6/1997 | Wozney et al. | |
| 5,645,592 A | 7/1997 | Nicolais et al. | |
| 5,648,467 A | 7/1997 | Kobayashi et al. | |
| 5,650,494 A | 7/1997 | Cerletti et al. | |
| 5,658,882 A | 8/1997 | Celeste et al. | |
| 5,661,007 A * | 8/1997 | Wozney et al. | 435/69.4 |
| 5,674,292 A | 10/1997 | Tucker et al. | |
| 5,688,678 A | 11/1997 | Hewick et al. | |
| 5,693,779 A | 12/1997 | Moos, Jr. et al. | |
| 5,700,664 A | 12/1997 | Bennett | |
| 5,700,774 A | 12/1997 | Hattersley et al. | |
| 5,700,911 A | 12/1997 | Wozney et al. | |
| 5,703,043 A * | 12/1997 | Celeste et al. | 514/12 |
| 5,728,679 A | 3/1998 | Celeste et al. | |
| 5,750,651 A | 5/1998 | Oppermann et al. | |
| 5,752,974 A | 5/1998 | Rhee et al. | |
| 5,756,457 A | 5/1998 | Wang et al. | |
| 5,786,421 A | 7/1998 | Tubo et al. | |
| 5,813,411 A | 9/1998 | Van Bladel et al. | |
| 5,827,733 A | 10/1998 | Lee et al. | |
| 5,846,931 A | 12/1998 | Hattersley et al. | |
| 5,849,880 A * | 12/1998 | Wozney et al. | 530/399 |
| 5,866,364 A | 2/1999 | Israel et al. | |
| 5,902,785 A * | 5/1999 | Hattersley et al. | 514/2 |
| 5,932,216 A | 8/1999 | Celeste et al. | |
| 5,935,594 A | 8/1999 | Ringeisen et al. | |
| 5,936,067 A | 8/1999 | Graham et al. | |
| 5,939,323 A | 8/1999 | Valentini et al. | |
| 5,939,388 A * | 8/1999 | Rosen et al. | 514/12 |
| 5,965,403 A | 10/1999 | Celeste et al. | |
| 5,972,368 A | 10/1999 | MacKay | |
| 5,986,058 A | 11/1999 | Lee et al. | |
| 6,001,352 A | 12/1999 | Boyan et al. | |
| 6,004,937 A | 12/1999 | Wood et al. | |
| 6,027,919 A | 2/2000 | Celeste et al. | |
| 6,034,061 A * | 3/2000 | Rosen et al. | 514/12 |
| 6,034,062 A | 3/2000 | Thies et al. | |
| 6,132,214 A | 10/2000 | Sohonen et al. | |
| 6,150,328 A * | 11/2000 | Wang et al. | 514/12 |
| 6,177,406 B1 * | 1/2001 | Wang et al. | 514/12 |
| 6,187,742 B1 | 2/2001 | Wozney et al. | |
| 6,190,880 B1 | 2/2001 | Israel et al. | |
| 6,207,813 B1 | 3/2001 | Wozney et al. | |
| 6,245,889 B1 | 6/2001 | Wang et al. | |
| 6,284,872 B1 | 9/2001 | Celeste et al. | |
| 6,287,816 B1 * | 9/2001 | Rosen et al. | 435/69.4 |
| 6,291,206 B1 | 9/2001 | Wozney et al. | |
| 6,331,612 B1 | 12/2001 | Celeste et al. | |
| 6,340,668 B1 | 1/2002 | Celeste et al. | |
| 6,432,919 B1 * | 8/2002 | Wang et al. | 514/12 |
| 6,437,111 B1 | 8/2002 | Wozney et al. | |
| 6,558,925 B2 | 5/2003 | Graham et al. | |
| 6,586,388 B2 | 7/2003 | Oppermann et al. | |
| 6,593,109 B1 | 7/2003 | Israel et al. | |

| | | | | | |
|---|---|---|---|---|---|
| 6,610,513 B2 | 8/2003 | Wozney et al. | WO | WO 92/22319 | 12/1992 |
| 6,613,744 B2 * | 9/2003 | Wozney et al. ............... 514/12 | WO | WO 93/00049 | 1/1993 |
| 6,620,406 B1 * | 9/2003 | Wozney et al. ............... 424/49 | WO | WO 93/00050 | 1/1993 |
| 6,623,934 B2 | 9/2003 | Celeste et al. | WO | WO 93/00432 | 1/1993 |
| 6,699,471 B2 | 3/2004 | Radici et al. | WO | WO 93/04692 | 3/1993 |
| 6,719,968 B2 | 4/2004 | Celeste et al. | WO | WO 93/05751 | 4/1993 |

FOREIGN PATENT DOCUMENTS

| | | | | | |
|---|---|---|---|---|---|
| EP | 0 052 510 | 5/1982 | WO | WO 93/06872 | 4/1993 |
| EP | 0 058 481 | 8/1982 | WO | WO 93/09228 | 5/1993 |
| EP | 0 121 976 | 10/1984 | WO | WO 93/09229 | 5/1993 |
| EP | 0 128 041 | 12/1984 | WO | WO 93/09802 | 5/1993 |
| EP | 0 148 155 | 7/1985 | WO | WO 93/13206 | 7/1993 |
| EP | 0 155476 | 9/1985 | WO | WO 93/16099 | 8/1993 |
| EP | 0 169 016 | 1/1986 | WO | WO 93/19177 | 9/1993 |
| EP | 0 177 343 | 4/1986 | WO | WO 93/20858 | 10/1993 |
| EP | 0 222 491 | 10/1986 | WO | WO 94/01557 | 1/1994 |
| EP | 0 212 474 | 3/1987 | WO | WO 94/03200 | 2/1994 |
| EP | 0 241 809 | 10/1987 | WO | WO 94/06449 | 3/1994 |
| EP | 0 336 760 | 4/1989 | WO | WO 94/11502 | 5/1994 |
| EP | 33 6760 | 6/1989 | WO | WO 94/15949 | 7/1994 |
| EP | 0 329 239 | 8/1989 | WO | WO 94/15965 | 7/1994 |
| EP | 4 165 78 A2 | 5/1990 | WO | WO 94/15966 | 7/1994 |
| EP | 0 394 418 | 10/1990 | WO | WO 94/21681 | 9/1994 |
| EP | 4 094 72 A1 | 11/1990 | WO | WO 94/24285 | 10/1994 |
| EP | 0 401 055 | 12/1990 | WO | WO 94/26892 | 11/1994 |
| EP | 0 409 472 | 1/1991 | WO | WO 94/26893 | 11/1994 |
| EP | 0 416 578 | 3/1991 | WO | WO 95/01801 | 1/1995 |
| EP | 0 429 570 | 6/1991 | WO | WO 95/01802 | 1/1995 |
| EP | 0 433 225 | 6/1991 | WO | WO 95/05846 | 3/1995 |
| EP | 0 512 844 | 11/1992 | WO | WO 95/07982 | 3/1995 |
| EP | 0 530 804 | 3/1993 | WO | WO 95/10539 | 4/1995 |
| EP | 0 531 448 | 11/1994 | WO | WO 95/10611 | 4/1995 |
| EP | 0 626 451 | 11/1994 | WO | WO 95/12664 | 5/1995 |
| EP | 0 688 869 | 12/1995 | WO | WO 95/15966 | 6/1995 |
| EP | 0 831 884 | 5/1996 | WO | WO 95/16035 | 6/1995 |
| EP | 0 313 578 | 8/1996 | WO | WO 95/33830 | 12/1995 |
| EP | 0 741 187 | 11/1996 | WO | WO 96/01845 | 1/1996 |
| EP | 0 592 562 | 1/1999 | WO | WO 96/02559 | 2/1996 |
| EP | 1 061 940 | 2/1999 | WO | WO 96/36710 | 11/1996 |
| EP | 0 536 186 | 11/2001 | WO | WO 96/38570 | 12/1996 |
| JP | 05-123390 A2 | 5/1993 | WO | WO 96/39170 | 12/1996 |
| JP | PAJ 03-345189 | 7/1993 | WO | WO 96/39203 | 12/1996 |
| JP | 05-277174 A2 | 10/1993 | WO | WO 96/40883 | 12/1996 |
| WO | WO 91/05802 | 5/1981 | WO | WO 07/15321 | 5/1997 |
| WO | WO 84/01106 | 3/1984 | WO | WO 97/22308 | 6/1997 |
| WO | WO 85/04173 | 9/1985 | WO | WO 97/34626 | 9/1997 |
| WO | WO 86/00525 | 1/1986 | WO | WO 97/40137 | 10/1997 |
| WO | WO 86/00639 | 1/1986 | WO | WO 97/45532 | 12/1997 |
| WO | WO 87/00528 | 1/1987 | WO | WO 97/48275 | 12/1997 |
| WO | WO 88/00205 * | 1/1988 | WO | WO 97/49412 | 12/1997 |
| WO | WO 89/09787 | 10/1989 | WO | WO 98/16641 | 4/1998 |
| WO | WO 89/09788 | 10/1989 | WO | WO 98/31788 | 7/1998 |
| WO | WO 89/10133 | 11/1989 | WO | WO 98/34951 | 8/1998 |
| WO | WO 89/10409 | 11/1989 | WO | WO 98/40113 | 9/1998 |
| WO | WO 90/03733 | 4/1990 | WO | WO 98/49296 | 11/1998 |
| WO | WO 90/11366 | 10/1990 | WO | WO 99/01159 | 1/1999 |
| WO | WO 91/02744 | 3/1991 | WO | WO 99/24070 | 5/1999 |
| WO | WO 91/04274 | 4/1991 | WO | W0 99/31120 | 6/1999 |
| WO | WO 91/05802 | 5/1991 | WO | WO 99/37320 | 7/1999 |
| WO | WO 91/10444 | 7/1991 | WO | WO 99/38543 | 8/1999 |
| WO | WO 91/17777 | 11/1991 | WO | WO 99/45949 | 9/1999 |
| WO | WO 91/18047 | 11/1991 | WO | WO 00/37124 | 6/2000 |
| WO | WO 91/18098 | 11/1991 | WO | WO 00/43781 A | 7/2000 |
| WO | WO 92/05198 | 4/1992 | | | |
| WO | WO 92/05199 | 4/1992 | | | |
| WO | WO 92/07004 | 4/1992 | | | |
| WO | WO 92/07073 | 4/1992 | | | |
| WO | WO 92/14481 | 9/1992 | | | |
| WO | WO 92/15323 | 9/1992 | | | |
| WO | WO 92/09697 | 11/1992 | | | |
| WO | WO 92/20793 | 11/1992 | | | |

OTHER PUBLICATIONS

Luyten et al., "Purification and Partial Amino Acid Sequence of Osteogenin, a Protein Initiating Bone Differentiation," *J. Biol. Chem.* 264: 13377-13380 (Aug. 15, 1989).

Sampath, et al., "Isolation of osteogenin, an extracellular matrix-associated, bone-inductive protein, by heparin affinity chromatography," *Proc. Natl Acad. Sci*, 84: 7109-7113 (1987).

Ozkaynak et al., "OP-1 cDNA encodes an osteogenic protein in the TGF-β family," *EMBO Journal*, v. 9 No. 7: 2085-2093 (1990).

Maniatis, T. et al., *Molecular Cloning, A Laboratory Mammal*, Cold Spring Harbor Laboratory, CSH. N.Y. (1982).
Suggs, S.V. et al., "Use of synthetic oligonucleotides as hybridization probes: Isolation of cloned cDNA sequences for human $\beta_2$-microglobulin," *Proc. Natl. Acad. Sci. USA.*, 501 78: pp. 6617 (1981).
Hammonds, et al. "Bone-inducing Activity of Mature BMP-2b Produced from a Hybrid BMP-2a/2b Precursor," *Mol. Endocrinol.* 5: 149-155 (1991).
Bowie, et al., "Deciphering the message in protein sequences: tolerance to amino acid substitutions," *Science*, 247:1306-10 (Mar. 16, 1990).
Alberts, et al. *Mol. Biol. Cell*, Garland Publishing, New York, NY: pp. 1142-1145 (Jan. 1994).
Sato et al., "Bone morphogenetic protein-induced cartilage development in tissue culture," *ClinicalOrthopaedics and Related Research*, 183: 180-7 (Mar. 1994).
Aiba et al., *Blood*, 90:3923-3030 (1997).
Alberts et al., *Molecular Biology of the Cell*, Third Ed., Garland Publishing, Inc., New York, NY, pp. 1142 (1983).
Amizuka et al., *J. Cell Biol.*, 126:1611-1623 (1994).
Attisano et al., *Cell*, 68:97-108 (1992).
Baird et al., *Biochem. Biophys. Res. Comm.*, 138:476-482 (1986).
Barres. B.A. et al., *Development*, 118:283-295 (1993).
Basler, K. et al., *Cell*, 73:687-702 (1993).
Beck et al., *Growth Factors*, 2:273-282 (1990).
Belo et al., *Mech. Devel.*, 68:45-57 (1997).
Bendig, *Genetic Engineering*, 7:91-127 (1988).
Biben et al., *Develop. Biol.*, 194:135-151 (1998).
Bignami et al., *Brain Res.*, 43:429-435 (1972).
Bignami, A. et al., *Plasticity and Regeneration of the Nervous System*, 197-206 (1991).
Bolton et al., *Biochem J.*, 133:529 (1973).
Border et al., *J. Clin. Invest.*, 90:1-7 (1992).
Bouwmeester et al., *Nature*, 382:595-601 (1996).
Bowen-Pope et al., *J. Biol. Chem.*, 237:5161 (1982).
Bowie et al., *Science*, 247:1306-1310 (1990).
Brown et al., *J. Immunol.*, 142:679 (1989).
Broxmeyer et al., *PNAS*, 85:9052 (1988).
Bruder et al., *J. Cell Biochem.*, 56:283-294 (1994).
Burt, D.W., *BBRC*, 184:590-595 (1992).
Campoccia et al., *Biomaterials*, 19:2101-27 (1998).
Caplan, A., *Bone Repair and Regeneration*, 21:429-435 (1994).
Celeste et al., *J. Bone Mineral Res.*, 9:suppl. 5136 (1994).
Celeste et al., *PNAS*, 87:9843-9847 (1990).
Chang et al., *J. Biol. Chem.*, 269:28227-28234 (1994).
Conlon et al., *Development*, 120:1919 (1994).
Conlon et al., *Development*, 111:969 (1991).
Collignon et al., *Nature*, 381:155 (1996).
Creighton, T.E., *Proteins: Structure and Molecular Principles*, W.H. Freeman and Co., New York (1983).
Cunningham et al., *PNAS*, 89:11740-11744 (1992).
Dagert et al., *Gene*, 6:23 (1979).
Dale et al., *EMBO J.*, 12:4471 (1993).
D'Alessandro et al., *Growth Factors*, 11:53-69 (1994).
D'Alessandro et al., *J. Bone Mineral Res.*, (6) Suppl: 1:S153 (1991).
DeWulf et al., *Endocrinology*, 136:2652-2663 (1995).
Dexter et al., *Nature*, 344:380 (1990).
DiLeone et al., *Genetics*, 148:401-408 (1998).
Doctor et al., *Dev. Biol.*, 151:591-605 (1992).
Ducy et al., *Kidney Intl.*, 57:2207-2214 (2000).
Dunn et al., *Cancer Cells*, 3:227-234 (1985).
Ebner et al., *Science*, 260:1344-1348 (1993).
Estevez et al., *Nature*, 365:644-649 (1993).
Eto et al., *Biochem. Biophys. Res. Comm.*, 142:1095 (1987).
Fainsod et al., *Mech. Dev.*, 1:39-50 (1997).
Fallon et al., *J. Cell Biol.*, 100:198-207 (1985).
Fenton et al., *Endocrinology*, 129:1762-1768 (1991).
Finch et al., *PNAS*, 94:6770-6775 (1997).
Frishchauf et al., *J. Mol. Biol.*, 170:827-842 (1983).
Frommel et al., *J. Mol. Evol.*, 24:33-257 (1985.
Gamer et al., *Develop. Biol.*, 208:222-232 (1999).
Geisert et al., *Develop. Biol.*, 143:335-345 (1991).

Gerhart et al., *Trans. Othop. Res. Soc.*, 16:172 (1991).
Gething et al., *Nature*, 293:620-625 (1981).
Gitelman et al., *J. Cell. Biol.*, 126:1595-1609 (1994).
Goodman, R., *Methods for Serum-Free Culture of Neuronal and Lymphoid Cells*, 23-36 (1984).
Gough et al., *EMBO J.*, 4:645-653 (1985).
Graham et al., *EMBO*, 15:6505-6515 (1996).
Graham et al., *Growth Factors*, 7:151-160 (1992).
Graham et al., *J. Biol. Chem.*, 269:4974-4978 (1994).
Graham et al., *Nature*, 344:442 (1990).
Guigon et al., *Chem. Abstracts*, 96:36, Abstract No. 115633h (1982).
Guigon et al., *Cancer Res.*, 42:638 (1982).
Hammonds et al., *Mol. Endocrin.*, 5:149-155 (1991).
Harrison et al., *Exp. Cell Res.*, 92:340-345 (1991).
Hashimoto et al., *J. Biol. Chem.*, 267:7203-7206 (1992).
He et al., *Develop. Dynamics*, 196:133-142 (1993).
Hebda et al., *J. Invest. Dermatol.*, 91:440-445 (1988).
Hefti et al., *J. Neurobiol.*, 25:1418-1435 (1994).
Hemmati-Brinvanlou et al., *Nature*, 359:609-614 (1992).
Hoang et al., *J. Biol. Chem.*, 271:26131-26137 (1996).
Hollnagel et al., *Calcified Tissue Int'l*, 56:430 (1995).
Hunkapiller et al., *Meth. Enzymol.*, 91:399-413 (1983).
Inouye et al., *Mol. Cell. Endocrinol.*, 90:1 (1992).
Iwasaki, *J. Biol. Chem.*, 271:17360-5 (1996).
Janowska-Wieczorek et al., *Biol. Abstracts, Reviews-Reports-Meetings*, 33:61402 (1987).
Jonhagen et al., *Dement. Cogn. Disord.*, 9:246-257 (1998).
Joyce et al, *J. Cell Biochem.*, Suppl.17E:136, Abstract R504 (1993).
Kalyani et al., *J. Neuroscience*, 18:7856-7869 (1998).
Karaplis et al., *Mol. Endocrin.*, 4:441-446 (1990).
Karaplis et al., *Genes & Development*, 8:277-289 (1994).
Katagiri et al, *J. Cell Biol.*, 127:1755-1766 (1994).
Kaufman et al., *Mol. Cell Biol.*, 2:1304-1319 (1982).
Kaufman et al., *Mol. Cell Biol.*, 5:1750-1759 (1985).
Kaufman et al., *J. Mol. Biol.*, 159:601-629 (1982).
Kaufman et al., *PNAS*, 82:689-693 (1985).
Kingsley et al., *Cell*, 71:399-410 (1992).
Kingsley et al., *Genes & Development*, 8:133-146 (1994).
Klein-Nulend et al., *Tissue Engineering*, 4:305-313 (1998).
Klein et al., *Brain Res.* 875:144-151 (2000).
Kliot et al., *Exper. Neur.*, 109:57-69 (1990).
Koenig et al., *Mol. Cell Biol.*, 14:5961-5974 (1994).
Koopman et al., *JBC*, 273:10103-10109 (1997).
Krueger, G.G., , *N. E. J. Med.*, 328:1845-1846 (1993).
LaPan et al., Program and Abstract, 13th Ann. Mtg of the AM Society of Bone and Min. Res., Aug. 24-28, p. 5153, Abstract No. 280, Mary Ann Liebert, Inc. NY (1991).
Lathe, J., *J. Mol. Biol.*, 183:1-12 (1985).
Lawn et al., *Cell*, 15:1157-1174 (1978).
Lefer et al., *PNAS*, 90:1018-22 (1993.
LeMaire et al., *Trends in Genetics*, 12:525-531 (1996).
Leslie M., *Nurse Practitioner*, 24:38, 41-8 (1999).
Lewin, *Science*, 237:1570 (1987).
Leyns et al., *Cell*, 88:747-756 (1997).
Lin et al., *Cell*, 68:775-785 (1992).
Lin et al., *Science*, 260:1130-1132 (1993).
Lipes et al., *PNAS*, 85:9704 (1988).
Lodish et al., *Mol. Cell Biol.*, 3rd Ed., W.H. Freeman & Co., p. 266 (1995).
Lopez-Coviella et al., *J. Physiol. Paris.*, 92:460-461 (1998).
Lopez-Coviella et al., *Science*, 289:313-316 (2000).
Lopez-Coviella et al., *Xth International Symposium on Cholinergic Mechanisms* (1998).
Lopez-Coviella et al., *Soc. Neurosci. Abstracts*, 25:517 (1999).
Lord et al., *Brit. J. Haematol.*, 34:441 (1976).
Lorimore et al., *Leuk. Res.*, 14:481-489 (1990).
Lowe et al., *Nature*, 381:158 (1996).
Lucas et al., *Differentiation*, 37:47-52 (1988).
Luthman et al., *Nucl. Acids Res.*, 11:1295-1308 (1983).
Luyten et al., *J. Biol. Chem.*, 264:13377-13380 (1989).
Luyten et al., *Exp. Cell. Res.*, 210(2):224-229 (1994).
Lyons et al., *PNAS*, 86:4554-4558 (1989).

Mangin et al., *PNAS*, 85:597-601 (1988).
Mangin et al., *Gene*, 95:195-202 (1990).
Maniatis et al., *Mol. Cloning, A Laboratory Manual, Cold Spring Harbor Laboraty*, CSH., N.Y.:310-323, 387-389 & 404-433 (1982).
Mantel et al., *PNAS*, 90:2232-2236 (1993).
Mansour et al., *J. Neurosci. Res.*, 25:300-377 (1990).
Marieb, E.N., *In Human Anatomy and Physiology, 2nd Ed.*, The Benjamin/Cummings Publishing Co., pp. 373-375 (1992).
Mark, *J. Cell. Biol.*, 130:701-10 (1995).
Marra et al., *EMBL Database*, Accession No. AA120122 (1996).
Martin et al., *Crit. Rev. Biochem. Mol. Biol.*, 26:377-395 (1991).
Mason et al., *Nature*, 318:659-663 (1985).
Massague et al., *Trends in Cell Biol.*, 4:172-178 (1994).
Massague et al., *Cell*, 69:1067-1070 (1992).
Massague et al., *Cell*, 49:437-438 (1987).
Mathews et al., *Cell*, 65:973-982 (1991).
Matsuzaki et al., *J. Biol. Chem.*, 268:12719-12723 (1993).
Matzuk et al., *Nature*, 360:313 (1992).
McConahey et al., *Int. Arch. Allergy*, 29:185-189 (1966).
McDonald et al., *Cell*, 73:421-424 (1993).
Miller et al., *J. Immunol.*, 143:2907 (1989).
Miller et al., *Genetic Engineering*, 8:277-298 (1986).
Miyazono et al., *Gen Bank Record No.* Z23154 (1993).
Morii et al., *J. Biol. Chem.*, 258:12749-12752 (1983).
Mullins et al., *Nature*, 303:856-858 (1984).
Nabeshima et al., *Alz Dis. And Assoc. Disord.* 14(Suppl. 1):S39-S46 (2000).
Nakamura et al., *J. Biol. Chem.*, 267:18924-18928 (1992).
Nakao et al., *Mol. Cell Biol.*, 10:3646-3658 (1990).
Nakatani T., *Jap. J. Clin. Med.*, 52:824-33 (1994).
Nathan et al., *J. Cell Biol.*, 113:981-986 (1991).
Neuhaus et al., *Mech. Dev.*, 80:181-184 (1999).
Nirschl, R., *American Orthopaedic Society for Sports Medicine*, Leadbetter, W. et al., eds, Ch. 13:577-585 (1989).
Ngo et al., Merz et al., eds., *Brickhauser*, Boston, Springer-Verlag, pp. 433-434 & 492-495 (1994).
Noble et al., *J. Neuroscience*, 4:1892-1903 (1984).
Obaru et al., *J. Biochem.*, 99:885 (1986).
Ogawa et al., *J. Biol. Chem.*, 267:14233 (1992).
Ohura et al., *J. Biomed. Mat. Res.*, 30:193-200 (1996).
Ohura et al., *J. Biomed. Mat. Res.*, 44: 168-175 (1999).
Okayama et al., *Mol. Cell Biol.*, 2:161-170 (1982).
Ozkaynak et al., *EMBO Journal*, 9:2085-2093 (1990).
Padgett et al., *Nature*, 325:81-84 (1987).
Paralkar, et al., *J. Cell Biol.*, 119:1721-1728 (1992).
Park et al., *J. Biol. Chem.*, 271:8161-9 (1996).
Patel et al., *Pharmacotherapy of Cognitive Impairment in Alzheimer's Disease: A Review*:81-95 (1992).
Perides et al., *J. Biol. Chem.*, 269:765-770 (1994).
Perides et al., *PNAS*, 89:10326-10330 (1992).
Peyron, J.G. *J. Rheumatol. Suppl.*, 27:2-3 (1991).
Pierce et al., *J. Clin. Investig.*, 96:1336-50 (1995).
Pollock, *J. Biol. Chem.*, 271:8008-14 (1996).
Pragnell et al., *Blood*, 72:196-201 (1988).
2001-2002 Progress Report on Alzheimer's Disease, *National Institute on Aging; NIH*:1-51 (2002).
Rabin et al., *Mol. Cell. Biol.*, 13:2203-2213 (1993).
Ralph et al., *Cancer Res.*, 37:546 (1977).
Ralph et al., *J. Immunol.*, 114:898 (1975).
Rattner et al., *PNAS*, 94:2859-2863 (1997).
Reddi, A. *JBJS*, 83-A:S1-1:S1-S6 (2001).
Reddi et al., *Osteoporosis, Academic Press*, pp. 281-287 (1996).
Reddi et al., *PNAS*, 69:1601 (1972).
Reeck, *Cell*, 50:667 (1987).
Roberts et al., *PNAS*, 83:4167-4171 (1986).
Roberston et al., *Biochem. Biophys. Res. Commun.*, 149:744-749 (1987).
Rodeo et al., *Orthopaedic Res. Soc.*, 41st Annual Mtg, Orlando, Florida, p. 288 (1995).
Rodeo, et al., *J. Bone Joint Surg.*, 75-A:1795-1803 (1993).
Rosen et al., *Trends in Genetics*, 8:97-102 (1992).
Rosen et al., *Connect Tissue Res.*, 20:313-9 (1989).
Rubin et al., *Science*, 287:2204-2215 (2000).

Rudinger, *Peptide Hormones*, Parsons (ed.), U Park Press, Baltimore:1-7 (1976).
Sakai et al., *PNAS*, 87:8378-8382 (1990).
Salic et al., *Development*, 124:4739-4748 (1997).
Sambrook et al., *Mol. Cloning: A Laboratory Manual, 2nd Ed.*, vols. 1, 2 and 3, Cold Spring Harbor Laboratory Press: Cold Spring Harbor, New York, USA (1989).
Sampath et al., *J. Biol Chem.*, 267:20352-20362 (1992).
Sampath et al., *J. Biol Chem.*, 265:13198-13205 (1990).
Sampath et al., *PNAS*, 84:7109-7113 (1987).
Sampath et al., *PNAS*, 80:6591-6595 (1983).
Sampath et al., *Exp. Cell. Res.*, 143:460-64 (1982).
Sato et al., *Clin. Orthopaedics Related Res.*, 183:180-187 (1984).
Saukkonon et al., *J. Exp. Med.*, 171:439 (1990).
Shubert et al., *Nature*, 344:868-870 (1990).
Schulz et al., *Principles of Protein Structure*, Springer-Verlag New York, Inc., New York:14-16 (1979).
Shah, et al., *J. Cell Sci.*, 108:985-1002 (1995).
Shimasaki et al., *PNAS*, 85:4218-4222 (1988).
Shipley et al., *Cancer Res.*, 46:2068-2071 (1986).
Shoda et al., *Growth Factors*, 8:165-172 (1993).
Smith et al., *Brain Res.*, 543:111-122 (1991).
Smith et al., *Dev. Biol.*, 138:377-390 (1990).
Smith et al., *J. Neurochem.*, 60:1453-1466 (1993).
Sompayrac et al., *PNAS*, 78:7575-7578 (1981).
Song et al., *Mol. Biol. Cell*, 5:384a (1994) and 34th Ann. Mtg of the American Soc. for Cell Biol., San Francisco, CA (1994).
Sporn et al., *Nature*, 332:217-219 (1988).
Sporn et al., *Science*, 233:532-534 (1986).
Storm et al., *Nature*, 368:639-642 (1994).
Sugino et al., *J. Biol. Chem.*, 268:15579 (1993).
Suggs et al., *PNAS*, 78:6613-6617 (1981).
Sumitomo et al., *Biochem. Biophys. Acta.*, 208.1 (1995).
Sumitomo et al., *DNA Sequence—J. DNA Sequence and Mapping* 3:297-302 (1993).
Suzuki et al., *Proc. Natl Acad Sci USA* 91:10255-59 (1994).
Tabas et al., *Genomics*, 9:283-289 (1991).
Takagi et al., *Clin. Orthopaed. Related Res.*, 171:224-231 (1982).
Taniguchi et al., *PNAS*, 77:5230-5233 (1980).
Tatusova et al., *FEMS Microbiol. Lett.*, 174:247-250 (1990).
Ten Dijke et al., *J. Biol. Chem.*, 269:16985-16988 (1994).
Ten Dijke et al., *EMBL Z22534* (Apr. 6, 1993).
Ten Dijke et al., *EMBL Sequence Database*, European Molecular Biology Laboratory (Basel, CH), Accesison No. Z22535 (1993).
Ten Dijke et al., *EMBL Sequence Database*, European Molecular Biology Laboratory (Basel, CH), Accesison No. Z22536 (1993).
Thies et al., *J. Bone Min. Res.*, 5:305 (1990).
Thies et al., *Endocrinol.*, 130:1318-1324 (1992).
Thomsen et al., *Trends in Genetics*, 13:209-211 (1997).
Thomsen et al., *Cell*, 74:433-441 (1993).
Tona et al., *J. Histochem. Cytochem.*, 41:591-599 (1993).
Toriumi et al., *Arch. Otolaryngol. Head Neck Surg.*, 117:1101-1112 (1991).
Tsuchida et al., *PNAS*, 90:11242-11246 (1993).
Tsukazaki et al., *Calcif. Tissue Int.*, 57:196-200 (1995).
Tuszynski, *Cell Transplantation*, 9:629-636 (2000).
Ueno et al., *PNAS*, 84:8282-8286 (1987).
Ulrich et al., *EMBO J.*, 3:361-364 (1984).
Urdal et al., *PNAS*, 81:6481-6485 (1984).
Urist et al., *Fed. Proceed.*, Bethesda, MD, US, 3:746 (1985).
Urist et al., *PNAS*, 81:371-375 (1984).
Urist et al., *Clin. Orthopaed. and Related Res.*, 187:277-280 (1984).
Urist et al., *Proc. Soc. Exper. Biol. & Med.*, 2:194 (1983).
Urist et al., *Science*, 220:680-686 (1983).
Urist et al., *PNAS*, 70:3511 (1973).
Urist et al., *Clin. Orthoped. Rel. Res.*, 214:295-304 (1986).
Urlaub et al., *PNAS*, 77:4216-20 (1980).
Vukicevic et al. *PNAS*, 93:9021-6 (1996).
Wall et al., *J. Cell Biol.*, 120:493-502 (1993).
Wang et al., *Cell*, 67:797-805 (1991).
Wang et al., *J. Cell Biochem.*, Suppl. 15, Part E, p. 161, Abstract Q020 (1991).
Wang et al., *PNAS*, 87:2220-2224 (1990).

Wang et al., *PNAS*, 85:9484-9488 (1988).
Wang, E.A., *Trends in Biotech.*, 11:379-383 (1993).
Wang et al., *Cell*, 88:757-766 (1997).
Wang et al., *Stroke*, 32:2170-2178 (2001).
Weeks et al., *Cell*, 51:861-867 (1987).
Wells, *Biochemistry*, 29:8509-8517 (1990).
Wharton et al., *PNAS*, 88:9214-9218 (1991).
Wolpe et al., *FASEB J.*, 3:2565-2573 (1989).
Wolpe et al., *J. Biochem. Suppl. O*, Abstract H141, 13 Part C:21 (1989).
Wolpe et al., *J. Exp. Med.*, 167:570 (1988).
Wong et al., *Science*, 228:810-815 (1985).
Woo et al., *PNAS*, 75:3688-3691 (1978).
Wood et al., *PNAS*, 82:1585-1588 (1985).
Wozney et al., *J. Cell Sci.*, Suppl. 13:149-156 (1990).
Wozney, *Mol. Reproduction & Develop.*, 32:160-167 (1992).
Wozney et al., *Science*, 242:1528-1534 (1988).
Wozney, J.M., *Prog. Growth Factor Res.*, 1:267-280 (1989).
Wozney et al., *Handbook of Exp. Pharm.*, eds., G.R. Mundy and T.J. Martin; Springer-Verlag, Berlin, Chapter 20, 107:725-748 (1993).
Wozney, *Cell. & Mol. Biol. Bone*, pp. 131-167 (1993) (Academic Press, Inc.).
Wozney et al., *J. Cell Biochem.*, Suppl. 16F:76 Abstract (1992).
Wozney *Spine*, 27:S2-S8 (2002).
Wright et al., *Leukemia Res.*, 4:537 (1980).
Wright et al., *Cell Tissue Kinet.*, 18:193 (1985).
Xu et al., *Proc Natl Acad Sci USA*, 91:7957-61 (1994).
Yamaguchi et al., *Nippon Rinsho*, 50:1932-1938 (1992).
Yamaji et al., *Biochem. Biophys. Res. Comm.*, 205:1944-1951 (1994).
Zipfel et al., *J. Immunol.*, 142:1582 (1989).
Zheng et al., *Path. Res. Pract.*, 188:1104-1121 (1992).
Zhou et al., *Nature*, 361:543-547 (1993).

\* cited by examiner

Figure 1

```
 (1)                    15                       30                          45
GGC CAC GAT GGG AAA GGA CAC CCT CTC CAC AGA AGA GAA  AAG CGG
 G   H   D   G   K   G   H   P   L   H   R   R   E    K   R 60                       75                          90
CAA GCA AAA CAC AAA CAG CGG AAA CGC CTC AAG TCC AGC TGT AAG
 Q   A   K   H   K   Q   R   K   R   L   K   S   S   C   K

(32)           105                      120                         135
AGA CAC CCT TTA TAT GTG GAC TTC AGT GAT GTG GGG TGG AAT GAC
 R   H   P   L   Y   V   D   F   S   D   V   G   W   N   D 150                      165                         180
TGG ATC GTT GCA CCG CCG GGG TAT CAT GCC TTT TAC TGC CAT GGG
 W   I   V   A   P   P   G   Y   H   A   F   Y   C   H   G 195                      210                         225
GAG TGC CCT TTT CCC CTG GCC GAT CAC CTT AAC TCC ACG AAT CAT
 E   C   P   F   P   L   A   D   H   L   N   S   T   N   H 240                      255                         270
GCC ATT CTC CAA ACT CTG GTC AAC TCA GTT AAC TCT AAG ATT CCC
 A   I   V   Q   T   L   V   N   S   V   N   S   K   I   P 385                      300                         315
AAG GCA TGC TGT GTC CCA ACA GAG CTC AGC GCC ATC TCC ATG CTG
 K   A   C   C   V   P   T   E   L   S   A   I   S   M   L 330                      345                         360
TAC CTT GAT GAG AAT GAG AAG GTG GTA TTA AAG AAC TAT CAG GAC
 Y   L   D   E   N   E   K   V   V   L   K   N   Y   Q   D
                                                 ___ ___ ___ ___

375              (129)       397            407
ATG GTT GTC GAG GGT TGT GGG TGT CGT TAGCACAGCA AAATAAAATA
 M   V   V   E   G   C   G   C   R
 ___ ___ ___ ___

417         427         437         447         457
TAAATATATA TATATATATA TTAGAAAAAC AGCAAAAAAA TCAAGTTGAC 467         477         487         497         507
ACTTTAATAT TTCCCAATGA AGACTTTATT TATGGAATGG AATGGAGAAA 517         527         537         547         557
AAGAAAAACA CAGCTATTTT GAAAACTATA TTTATATCTA CCGAAAAGAA 567         577         587
GTTGGGAAAA CAAATATTTT AATCAGAGAA TTATT
```

Figure 2

```
          10         20         30         40         50         60         70
   GTCGACTCTA GAGTGTGTGT CAGCACTTGG CTGGGGACTT CTTGAACTTG CAGGGAGAAT AACTTGCGCA 80         90        100        110        120        130        140
   CCCCACTTTG CGCCGGTGCC TTTGCCCCAG CGGAGCCTGC TTCGCCATCT CCGAGCCCCA CCGCCCCTCC 150        160        170        180        190        200        210
   ACTCCTCGGC CTTGCCCGAC ACTGAGACGC TGTTCCCAGC GTGAAAAGAG AGACTGCGCG GCCGGCACCC 220        230        240        250        260        270        280
   GGGAGAAGGA GGAGGCAAAG AAAAGGAACG GACATTCGGT CCTTGCGCCA GGTCCTTTGA CCAGAGTTTT 290        300        310        320        330        340        350
   TCCATGTGGA CGCTCTTTCA ATGGACGTGT CCCCGCGTGC TTCTTAGACG GACTGCGGTC TCCTAAAGGT
```

```
         (1)                   370                   385                   400
   CGACC ATG GTG GCC GGG ACC CGC TGT CTT CTA GCG TTG CTG CTT CCC CAG GTC
         MET Val Ala Gly Thr Arg Cys Leu Leu Ala Leu Leu Leu Pro Gln Val 415                   430                   445
   CTC CTG GGC GGC GCG GCT GGC CTC GTT CCG GAG CTG GGC CGC AGG AAG TTC GCG
   Leu Leu Gly Gly Ala Ala Gly Leu Val Pro Glu Leu Gly Arg Arg Lys Phe Ala
                                  (24)

460                   475                   490                   505
   GCG GCG TCG TCG GGC CGC CCC TCA TCC CAG CCC TCT GAC GAG GTC CTG AGC GAG
   Ala Ala Ser Ser Gly Arg Pro Ser Ser Gln Pro Ser Asp Glu Val Leu Ser Glu 520                   535                   550                   565
   TTC GAG TTG CGG CTG CTC AGC ATG TTC GGC CTG AAA CAG AGA CCC ACC CCC AGC
   Phe Glu Leu Arg Leu Leu Ser MET Phe Gly Leu Lys Gln Arg Pro Thr Pro Ser 580                   595                   610
   AGG GAC GCC GTG GTG CCC CCC TAC ATG CTA GAC CTG TAT CGC AGG CAC TCA GGT
   Arg Asp Ala Val Val Pro Pro Tyr Met Leu Asp Leu Tyr Arg Arg His Ser Gly 625                   640                   655                   670
   CAG CCG GGC TCA CCC GCC CCA GAC CAC CGG TTG GAG AGG GCA GCC AGC CGA GCC
   Gln Pro Gly Ser Pro Ala Pro Asp His Arg Leu Glu Arg Ala Ala Ser Arg Ala
```

Figure 2 (Con't)

```
           685                    700                    715
AAC ACT GTG CGC AGC TTC CAC CAT GAA GAA TCT TTG GAA GAA CTA CCA GAA ACG
Asn Thr Val Arg Ser Phe His His Glu Glu Ser Leu Glu Glu Leu Pro Glu Thr 730                    745                    760                    775
AGT GGG AAA ACA ACC CGG AGA TTC TTC TTT AAT TTA AGT TCT ATC CCC ACG GAG
Ser Gly Lys Thr Thr Arg Arg Phe Phe Phe Asn Leu Ser Ser Ile Pro Thr Glu 790                    805                    820           835
GAG TTT ATC ACC TCA GCA GAG CTT CAG GTT TTC CGA GAA CAG ATG CAA GAT GCT
Glu Phe Ile Thr Ser Ala Glu Leu Gln Val Phe Arg Glu Gln Met Gln Asp Ala 850                    865                    880
TTA GGA AAC AAT AGC AGT TTC CAT CAC CGA ATT AAT ATT TAT GAA ATC ATA AAA
Leu Gly Asn Asn Ser Ser Phe His His Arg Ile Asn Ile Tyr Glu Ile Ile Lys 895                    910                    925                940
CCT GCA ACA GCC AAC TCG AAA TTC CCC GTG ACC AGA CTT TTG GAC ACC AGG TTG
Pro Ala Thr Ala Asn Ser Lys Phe Pro Val Thr Arg Leu Leu Asp Thr Arg Leu 955                    970                    985
GTG AAT CAG AAT GCA AGC AGG TGG GAA AGT TTT GAT GTC ACC CCC GCT GTG ATG
Val Asn Gln Asn Ala Ser Arg Trp Glu Ser Phe Asp Val Thr Pro Ala Val MET 1000                   1015                   1030                   1045
CGG TGG ACT GCA CAG GGA CAC GCC AAC CAT GGA TTC GTG GTG GAA GTG GCC CAC
Arg Trp Thr Ala Gln Gly His Ala Asn His Gly Phe Val Val Glu Val Ala His 1060                   1075                   1090              1105
TTG GAG GAG AAA CAA GGT GTC TCC AAG AGA CAT GTT AGG ATA AGC AGG TCT TTG
Leu Glu Glu Lys Gln Gly Val Ser Lys Arg His Val Arg Ile Ser Arg Ser Leu
                                                                    (247)

1120                   1135                   1150
CAC CAA GAT GAA CAC AGC TGG TCA CAG ATA AGG CCA TTG CTA GTA ACT TTT GGC
His Gln Asp Glu His Ser Trp Ser Gln Ile Arg Pro Leu Leu Val Thr Phe Gly
                                                                (266)

1165                   1180                   1195              1210
CAT GAT GGA AAA GGG CAT CCT CTC CAC AAA AGA GAA AAA CGT CAA GCC AAA CAC
His Asp Gly Lys Gly His Pro Leu His Lys Arg Glu Lys Arg Gln Ala Lys His
                                                                      (283)

1225                   1240            (299)1255
AAA CAG CGG AAA CGC CTT AAG TCC AGC TGT AAG AGA CAC CCT TTG TAC GTG GAC
Lys Gln Arg Lys Arg Leu Lys Ser Ser Cys Lys Arg His Pro Leu Tyr Val Asp 1270                   1285                   1300                   1315
TTC AGT GAC GTG GGG TGG AAT GAC TGG ATT GTG GCT CCC CCG GGG TAT CAC GCC
Phe Ser Asp Val Gly Trp Asn Asp Trp Ile Val Ala Pro Pro Gly Tyr His Ala
```

Figure 2 (con't)

```
        1330                1345                1360                1375
TTT TAC TGC CAC GGA GAA TGC CCT TTT CCT CTG GCT GAT CAT CTG AAC TCC ACT
Phe Tyr Cys His Gly Glu Cys Pro Phe Pro Leu Ala Asp His Leu Asn Ser Thr 1390                1405                1420
AAT CAT GCC ATT GTT CAG ACG TTG GTC AAC TCT GTT AAC TCT AAG ATT CCT AAG
Asn His Ala Ile Val Gln Thr Leu Val Asn Ser Val Asn Ser Lys Ile Pro Lys 1435                1450                1465                1480
GCA TGC TGT GTC CCG ACA GAA CTC AGT GCT ATC TCG ATG CTG TAC CTT GAC GAG
Ala Cys Cys Val Pro Thr Glu Leu Ser Ala Ile Ser MET Leu Tyr Leu Asp Glu 1495                1510                1525
AAT GAA AAG GTT GTA TTA AAG AAC TAT CAG GAC ATG GTT GTG GAG GGT TGT GGG
Asn Glu Lys Val Val Leu Lys Asn Tyr Gln Asp MET Val Val Glu Gly Cys Gly
                                   ‾‾‾ ‾‾‾ ‾‾‾ ‾‾‾ ‾‾‾ ‾‾‾ ‾‾‾ ‾‾‾ ‾‾‾

1540(396)       1553        1563        1573        1583        1593        1603
TGT CGC TAGTACAGCA AAATTAAATA CATAAATATA TATATATATA TATATTTTAG AAAAAAGAAA
Cys Arg
```

AAAA

Figure 3

```
         10         20         30         40         50         60         70
CTCTAGAGGG CAGAGGAGGA GGGAGGGAGG GAAGGAGCGC GGAGCCCGGC CCGGAAGCTA GGTGAGTGTG 80         90        100        110        120        130        140
GCATCCGAGC TGAGGGACGC GAGCCTGAGA CGCCGCTGCT GCTCCGGCTG AGTATCTAGC TTGTCTCCCC 150        160        170        180        190        200        210
GATGGGATTC CCGTCCAAGC TATCTCGAGC CTGCAGCGCC ACAGTCCCCG GCCCTCGCCC AGGTTCACTG 220        230        240        250        260        270        280
CAACCGTTCA GAGGTCCCCA GGAGCTGCTG CTGGCGAGCC CGCTACTGCA GGGACCTATG GAGCCATTCC 290        300        310        320        330        340        350
GTAGTGCCAT CCCGAGCAAC GCACTGCTGC AGCTTCCCTG AGCCTTTCCA GCAAGTTTGT TCAAGATTGG 360        370        380        390        400        (1)
CTGTCAAGAA TCATGGACTG TTATTATATG CCTTGTTTTC TGTCAAGACA CC ATG ATT CCT
                                                         MET Ile Pro
```

```
    417                     432                     447                     462
GGT AAC CGA ATG CTG ATG GTC GTT TTA TTA TGC CAA GTC CTG CTA GGA GGC GCG
Gly Asn Arg MET Leu MET Val Val Leu Leu Cys Gln Val Leu Leu Gly Gly Ala 477                     492                     507
AGC CAT GCT AGT TTG ATA CCT GAG ACG GGG AAG AAA AAA GTC GCC GAG ATT CAG
Ser His Ala Ser Leu Ile Pro Glu Thr Gly Lys Lys Lys Val Ala Glu Ile Gln 522                     537                     552                     567
GGC CAC GCG GGA GGA CGC CGC TCA GGG CAG AGC CAT GAG CTC CTG CGG GAC TTC
Gly His Ala Gly Gly Arg Arg Ser Gly Gln Ser His Glu Leu Leu Arg Asp Phe 582                     597                     612                     627
GAG GCG ACA CTT CTG CAG ATG TTT GGG CTG CGC CGC CGC CCG CAG CCT AGC AAG
Glu Ala Thr Leu Leu Gln MET Phe Gly Leu Arg Arg Arg Pro Gln Pro Ser Lys 642                     657                     672
AGT GCC GTC ATT CCG GAC TAC ATG CGG GAT CTT TAC CGG CTT CAG TCT GGG GAG
Ser Ala Val Ile Pro Asp Tyr MET Arg Asp Leu Tyr Arg Leu Gln Ser Gly Glu
```

Figure 3 (con't)

```
     687                          702                          717                          732
GAG GAG GAA GAG CAG ATC CAC AGC ACT GGT CTT GAG TAT CCT GAG CGC CCG GCC
Glu Glu Glu Glu Gln Ile His Ser Thr Gly Leu Glu Tyr Pro Glu Arg Pro Ala 747                          762                          777
AGC CGG GCC AAC ACC GTG AGG AGC TTC CAC CAC GAA GAA CAT CTG GAG AAC ATC
Ser Arg Ala Asn Thr Val Arg Ser Phe His His Glu Glu His Leu Glu Asn Ile 792                          807                          822                          837
CCA GGG ACC AGT GAA AAC TCT GCT TTT CGT TTC CTC TTT AAC CTC AGC AGC ATC
Pro Gly Thr Ser Glu Asn Ser Ala Phe Arg Phe Leu Phe Asn Leu Ser Ser Ile 852                          867                          882                          897
CCT GAG AAC GAG GTG ATC TCC TCT GCA GAG CTT CGG CTC TTC CGG GAG CAG GTG
Pro Glu Asn Glu Val Ile Ser Ser Ala Glu Leu Arg Leu Phe Arg Glu Gln Val 912                          927                          942
GAC CAG GGC CCT GAT TGG GAA AGG GGC TTC CAC CGT ATA AAC ATT TAT GAG GTT
Asp Gln Gly Pro Asp Trp Glu Arg Gly Phe His Arg Ile Asn Ile Tyr Glu Val 957                          972                          987                          1002
ATG AAG CCC CCA GCA GAA GTG GTG CCT GGG CAC CTC ATC ACA CGA CTA CTG GAC
MET Lys Pro Pro Ala Glu Val Val Pro Gly His Leu Ile Thr Arg Leu Leu Asp 1017                         1032                         1047
ACG AGA CTG GTC CAC CAC AAT GTG ACA CGG TGG GAA ACT TTT GAT GTG AGC CCT
Thr Arg Leu Val His His Asn Val Thr Arg Trp Glu Thr Phe Asp Val Ser Pro 1062                         1077                         1092                         1107
GCG GTC CTT CGC TGG ACC CGG GAG AAG CAG CCA AAC TAT GGG CTA GCC ATT GAG
Ala Val Leu Arg Trp Thr Arg Glu Lys Gln Pro Asn Tyr Gly Leu Ala Ile Glu 1122                         1137                         1152                         1167
GTG ACT CAC CTC CAT CAG ACT CGG ACC CAC CAG GGC CAG CAT GTC AGG ATT AGC
Val Thr His Leu His Gln Thr Arg Thr His Gln Gly Gln His Val Arg Ile Ser 1182                         1197                         1212
CGA TCG TTA CCT CAA GGG AGT GGG AAT TGG GCC CAG CTC CGG CCC CTC CTG GTC
Arg Ser Leu Pro Gln Gly Ser Gly Asn Trp Ala Gln Leu Arg Pro Leu Leu Val 1227                         1242                         1257                         1272
ACC TTT GGC CAT GAT GGC CGG GGC CAT GCC TTG ACC CGA CGC CGG AGG GCC AAG
Thr Phe Gly His Asp Gly Arg Gly His Ala Leu Thr Arg Arg Arg Arg Ala Lys 1287                         1302                         1317
CGT AGC CCT AAG CAT CAC TCA CAG CGG GCC AGG AAG AAG AAT AAG AAC TGC CGG
Arg Ser Pro Lys His His Ser Gln Arg Ala Arg Lys Lys Asn Lys Asn Cys Arg
    (293)
```

Figure 3 (con't)

```
1332(311)            1347                 1362                 1377
CGC CAC TCG CTC TAT GTG GAC TTC AGC GAT GTG GGC TGG AAT GAC TGG ATT GTG
Arg His Ser Leu Tyr Val Asp Phe Ser Asp Val Gly Trp Asn Asp Trp Ile Val 1392                 1407                 1422                 1437
GCC CCA CCA GGC TAC CAG GCC TTC TAC TGC CAT GGG GAC TGC CCC TTT CCA CTG
Ala Pro Pro Gly Tyr Gln Ala Phe Tyr Cys His Gly Asp Cys Pro Phe Pro Leu 1452                 1467                 1482
GCT GAC CAC CTC AAC TCA ACC AAC CAT GCC ATT GTG CAG ACC CTG GTC AAT TCT
Ala Asp His Leu Asn Ser Thr Asn His Ala Ile Val Gln Thr Leu Val Asn Ser 1497                 1512                 1527                 1542
GTC AAT TCC AGT ATC CCC AAA GCC TGT TGT GTG CCC ACT GAA CTG AGT GCC ATC
Val Asn Ser Ser Ile Pro Lys Ala Cys Cys Val Pro Thr Glu Leu Ser Ala Ile 1557                 1572                 1587
TCC ATG CTG TAC CTG GAT GAG TAT GAT AAG GTG GTA CTG AAA AAT TAT CAG GAG
Ser MET Leu Tyr Leu Asp Glu Tyr Asp Lys Val Val Leu Lys Asn Tyr Gln Glu 1602                 1617         (408)   1636       1646        1656
ATG GTA GTA GAG GGA TGT GGG TGC CGC TGAGATCAGG CAGTCCTTGA GGATAGACAG
MET Val Val Glu Gly Cys Gly Cys Arg 1666       1676       1686       1696       1706       1716       1726
ATATACACAC CACACACACA CACCACATAC ACCACACACA CACGTTCCCA TCCACTCACC CACACACTAC 1736       1746       1756       1766       1776       1786       1796
ACAGACTGCT TCCTTATAGC TGGACTTTTA TTTAAAAAAA AAAAAAAAAA AATGGAAAAA ATCCCTAAAC 1806       1816       1826       1836       1846       1856       1866
ATTCACCTTG ACCTTATTTA TGACTTTACG TGCAAATGTT TTGACCATAT TGATCATATA TTTTGACAAA 1876       1886       1896       1906       1916       1926       1936
ATATATTTAT AACTACGTAT TAAAAGAAAA AAATAAAATG AGTCATTATT TTAAAAAAAA AAAAAAAACT

1946
CTAGAGTCGA CGGAATTC
```

METHODS OF TREATMENT OF PERIODONTAL DISEASE

This application is a continuation of U.S. Ser. No. 09/804,625 filed Mar. 9, 2001 (pending); which is a continuation of U.S. Ser. No. 08/925,779 filed Sep. 9, 1997 (now U.S. Pat. No. 6,245,889); which is a continuation of U.S. Ser. No. 07/721,847 filed Jun. 14, 1991 (now U.S. Pat. No. 6,150,328). U.S. Ser. No. 07/721,847 is a continuation-in-part of two applications (U.S. Ser. Nos. 07/493,272 filed Mar. 14, 1990 (now abandoned) and 07/655,579 filed Mar. 18, 1991 (now U.S. Pat. No. 5,618,924). U.S. Ser. Nos. 07/493,272 is a continuation-in-part of two applications (U.S. Ser. Nos. 07/406,217 filed Sep. 12, 1989 (now abandoned) and 07/378,537 filed Jul. 11, 1989 (now U.S. Pat. No. 5,166,058). U.S. Ser. No. 07/655,579 is a divisional of U.S. Ser. No. 07/179,100 filed Apr. 8, 1988 (now U.S. Pat. No. 5,013,649), while U.S. Ser. No. 07/378,537 is a continuation-in-part of U.S. Ser. No. 07/179,100 filed Apr. 8, 1988, now U.S. Pat. No. 5,013,649. Applicants claim priority to all of these applications.

The present invention relates to a novel family of purified proteins designated BMP-2 and BMP-4 proteins and processes for obtaining and producing them. These proteins may be used to induce bone and/or cartilage formation and in wound healing and tissue repair.

BMP-2 and BMP-4 proteins have previously been referred to collectively as BMP-2 proteins (BMP-2 previously referred to as BMP-2A or BMP-2 Class I and BMP-4 as BMP-2B or BMP-2 Class II).

Human BMP-2 proteins are characterized by an amino acid sequence comprising amino acid #299 (His, Pro, Leu . . . )—#396 (Arg) of FIG. 2 (SEQ ID NO: 4). Human BMP-2 proteins are further characterized as dimers of BMP-2 subunits. Mature BMP-2 is characterized by comprising amino acid #283 (Gln, Ala, Lys . . . )—#396 (Arg) of FIG. 2. Mature BMP-2 is further characterized as a disulfide linked dimer wherein each subunit comprises amino acids #283-#396 of FIG. 2 (SEQ ID NO: 4).

Human BMP-2 may be produced by culturing a cell transformed with a DNA sequence comprising the nucleotide coding sequence from nucleotide #356 to #1543 as shown in FIG. 2 (SEQ ID NO: 3) and recovering and purifying from the culture medium a protein comprising amino acid #299 to #396 as shown in FIG. 2 (SEQ ID NO: 4), substantially free from other proteinaceous materials with which it is co-produced. Human BMP-2 is characterized by the ability to induce bone formation. Human BMP-2 is further characterized by the ability to induce cartilage formation. Human BMP-2 may be further characterized by the ability to demonstrate cartilage and/or bone formation activity in the rat bone formation assay described below. In preferred embodiments, the proteins of the invention demonstrate activity in this assay at a concentration of 10 μg-500 μg/gram of bone. BMP-2 proteins may be characterized by the ability of 1 μg of the protein to score at least +2 in the rat bone formation assay of Example III using the modified scoring method described in Example VII.

The bovine BMP-2 protein is a member of the family of BMP-2 proteins of the invention. Bovine BMP-2 proteins comprise the amino acid sequence represented by amino acid #32 to amino acid #129 of FIG. 1 (SEQ ID NO: 2). These proteins are capable of inducing the formation of cartilage and/or bone. Bovine BMP-2 may be further characterized by the ability to demonstrate cartilage and/or bone formation activity in the rat bone formation assay described below. In preferred embodiments, the proteins of the invention demonstrate activity in this assay at a concentration of 10 μg-500 μg/gram of bone. These proteins may be characterized by the ability of 1 μg of the protein to score at least +2 in the rat bone formation assay described in Example III using the modified scoring method as described in Example VII.

Human BMP-4 proteins are characterized by an amino acid sequence comprising amino acids #311 (His, Ser, Leu . . . )—#408 (Arg) as shown in FIG. 3 (SEQ ID NO: 6). Mature BMP-4 comprises amino acids #293 (Ser, Pro, Lys . . . )—#408 (Arg) of FIG. 3. BMP-4 proteins are further characterized as dimers of BMP-4 subunits. Mature BMP-4 is further characterized as a disulfide linked dimer wherein each subunit comprises amino acids #293-#408 of FIG. 3 (SEQ ID NO: 6).

BMP-4 may be produced by culturing a cell transformed with a DNA sequence comprising the nucleotide coding sequence from nucleotide #403 to nucleotide #1626 substantially as shown in FIG. 3 (SEQ ID NO: 5) and recovering and purifying from the culture medium a protein containing the amino acid sequence from amino acid #311 to #408 as shown in FIG. 3 (SEQ ID NO: 6) substantially free from other proteinaceous materials with which it is co-produced. BMP-4 proteins are capable of inducing the formation of bone. BMP-4 proteins are capable of inducing formation of cartilage. BMP-4 proteins are further characterized by the ability to demonstrate cartilage and/or bone formation activity in the rat bone formation assay described below. In preferred embodiments, the proteins of the invention demonstrate activity in this assay at a concentration of 10 μg-500 μg/gram of bone. These proteins may be characterized by the ability of 1 μg of the protein to score at least +2 in the rat bone formation assay of Example III using the modified scoring method described in Example VII.

Another aspect of the invention provides pharmaceutical compositions containing a therapeutically effective amount of a BMP-2 or BMP-4 protein in a pharmaceutically acceptable vehicle or carrier. These compositions of the invention may be utilized in the formation of cartilage. These compositions may further be utilized in the formation of bone. They may also be used for wound healing and tissue repair. In further embodiments the compositions of the invention may be utilized for neuronal survival.

Further compositions of the invention may comprise a therapeutically effective amount of BMP-2 and BMP-4 in a pharmaceutically acceptable vehicle. Compositions of the invention may further include, in addition to a BMP-2 or BMP-4 protein, at least one other therapeutically useful agent such as the BMP proteins BMP-1, BMP-3, BMP-5, BMP-6, BMP-7, and BMP-8 disclosed respectively in co-owned U.S. patent application Ser. No. 655,578, Ser. No. 179,197, Ser. No. 370,547, Ser. No. 370,544 Ser. No. 370,549, and Ser. No. 525,357. The compositions of the invention may comprise, in addition to a BMP-2 or BMP-4 protein, other therapeutically useful agents including growth factors such as epidermal growth factor (EGF), fibroblast growth factor (FGF), and transforming growth factor (TGF-α and TGF-β). The compositions may also include an appropriate matrix for instance, for supporting the composition and providing a surface for bone and/or cartilage growth. The matrix may provide slow release of the BMP protein and/or the appropriate environment for presentation of the BMP protein.

The BMP-2 and BMP-4 compositions may be employed in methods for treating a number of bone and/or cartilage defects, periodontal disease and various types of wounds.

These methods, according to the invention, entail administering to a patient needing such bone and/or cartilage formation wound healing or tissue repair, an effective amount of a BMP-2 or BMP-4 protein. These methods may also entail the administration of a protein of the invention in conjunction with at least one of the novel BMP proteins disclosed in the co-owned applications described above. In addition, these methods may also include the administration of a BMP-2 or BMP-4 protein with other growth factors.

Still a further aspect of the invention are DNA sequences encoding a BMP-2 or BMP-4 protein. Such sequences include the sequence of nucleotides in a 5' to 3' direction illustrated in FIGS. 1 through 3 (SEQ ID NO: 1, 3, and 5) or DNA sequences which hybridize under stringent conditions with the DNA sequences of FIGS. 1-3 and encode a protein having the ability to induce the formation of cartilage and/or bone. Finally, allelic or other variations of the sequences of FIGS. 1 through 3, whether such nucleotide changes result in changes in the peptide sequence or not, are also included in the present invention.

A further aspect of the invention entails a vector comprising a DNA sequence as described above in operative association with an expression control sequence therefor. Such vector may be employed in a novel process for producing a BMP-2 or BMP-4 protein of the invention in which a cell line transformed with a DNA sequence encoding a BMP-2 or BMP-4 protein in operative association with an expression control sequence therefor, is cultured in a suitable culture medium and a BMP-2 or BMP-4 protein is recovered and purified therefrom. This claimed process may employ a number of known cells both prokaryotic and eukaryotic as host cells for expression of the polypeptide.

Other aspects and advantages of the present invention will be apparent upon consideration of the following detailed description and preferred embodiments thereof.

BRIEF DESCRIPTION OF THE DRAWING

FIG. 1 comprises partial DNA and derived amino acid sequence of bovine BMP-2 from bacteriophage lambda bP-21, ATCC #40310 further described below.

FIG. 2 sets forth the DNA and derived amino acid sequence of human BMP-2 from lambda U2OS-39, ATCC #40345 further described below.

FIG. 3 sets forth the DNA and derived amino acid sequence of human BMP-4 from lambda U2OS-3, ATCC #40342 further described below.

DETAILED DESCRIPTION OF THE INVENTION

BMP-2 proteins are characterized by an amino acid sequence comprising amino acid #299-#396 of FIG. 2 (SEQ ID NO: 4). BMP-2 proteins are further characterized as dimers of BMP-2 subunits. Mature BMP-2 comprises amino acids #283-#396 of FIG. 2. Mature BMP-2 is further characterized as a disulfide linked homodimer wherein each subunit comprises amino acids #283-#396 of FIG. 2 (SEQ ID NO: 4).

The purified human BMP-2 proteins of the present invention are produced by culturing a host cell transformed wth a DNA sequence comprising the DNA coding sequence of FIG. 2 (SEQ ID NO: 3) from nucleotide #356 to nucleotide #1543 and recovering and purifying from the culture medium a protein which contains the 97 amino acid sequence or a substantially homologous sequence as represented by amino acid #299 to #396 of FIG. 2 (SEQ ID NO: 4). The BMP-2 proteins recovered from the culture medium are purified by isolating them from other proteinaceous materials with which they are co-produced and from other contaminants present.

BMP-4 proteins are characterized by an amino acid sequence comprising amino acids #311-#408 as shown in FIG. 3 (SEQ ID NO: 6). BMP-4 proteins are further characterized as dimers of BMP-4 subunits. Mature BMP-4 comprises amino acids #293-#408 of FIG. 3. Mature BMP-4 is further characterized as a disulfide linked homodimer each subunit comprising amino acids #293-#408 of FIG. 3 (SEQ ID NO: 6).

The purified BMP-4 proteins are produced by culturing a host cell transformed with a DNA sequence comprising the DNA coding sequence of FIG. 3 (SEQ ID NO: 5) from nucleotide #403 to nucleotide #1626 and recovering and purifying from the culture medium a protein comprising the amino acid sequence from amino acid #311 to #408 of FIG. 3 (SEQ ID NO: 6). The BMP-4 proteins recovered from the culture medium are purified by isolating them from other proteinaceous materials with which they are co-produced and from other contaminants present.

BMP-2 and BMP-4 proteins are characterized by the ability to induce the formation of bone. They are further characterized by the ability to induce the formation of cartilage. BMP-2 and BMP-4 proteins may be further characterized by the ability to demonstrate cartilage and/or bone formation activity in the rat bone formation assay described below. In preferred embodiments, the proteins of the invention demonstrate activity in this rat bone formation assay at a concentration of 10 μg-500 μg/gram of bone. These proteins may be characterized by the ability of 1 μg of the protein to score at least +2 in the rat bone formation assay using the modified scoring method described in Example VII.

The BMP-2 and BMP-4 proteins provided herein also include factors encoded by the sequences similar to those of FIGS. 1-3 (SEQ ID NO: 1, 3, 5), but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of FIGS. 1-3. These sequences, by virtue of sharing primary, secondary, or tertiary structural and conformational characteristics with bone growth factor polypeptides of FIGS. 1-3 may possess bone growth factor biological properties in common therewith. Thus, they may be employed as biologically active substitutes for naturally-occurring BMP-2 and BMP-4 polypeptides in therapeutic processes.

Other specific mutations of the sequences of BMP-2 and BMP-4 proteins described herein involve modifications of at least one of the glycosylation sites. The absence of glycosylation or only partial glycosylation results from amino acid substitution or deletion at asparagine-linked glycosylation recognition sites present in the sequences of BMP-2 and BMP-4 proteins shown in FIGS. 1-3. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

The present invention also encompasses the novel DNA sequences, free of association with DNA sequences encoding other proteinaceous materials, and coding on expression for BMP-2 and BMP-4 proteins. These DNA sequences include those depicted in FIGS. 1-3 in a 5' to 3' direction and those sequences which hybridize under stringent hybridization conditions [see, T. Maniatis et al, *Molecular Cloning (A Laboratory Manual)*, Cold Spring Harbor Laboratory (1982), pages 387 to 389] to the DNA sequences of FIGS. 1-3 and encode a protein having cartilage and/or bone inducing activity.

Similarly, DNA sequences which code for BMP-2 and BMP-4 polypeptides coded for by the sequences of FIGS. 1-3, but which differ in codon sequence due to the degeneracies of the genetic code or allelic variations (naturally-occurring base changes in the species population which may or may not result in an amino acid change) also encode the novel factors described herein. Variations in the DNA sequences of FIGS. 1-3 which are caused by point mutations or by induced modifications (including insertion, deletion, and substitution) to enhance the activity, half-life or production of the polypeptides encoded thereby are also encompassed in the invention.

Another aspect of the present invention provides a novel method for producing BMP-2 and BMP-4 proteins. The method of the present invention involves culturing a suitable cell line, which has been transformed with a DNA sequence coding on expression for a BMP-2 or BMP-4 protein, under the control of known regulatory sequences. The transformed host cells are cultured and the BMP-2 or BMP-4 proteins recovered and purified from the culture medium. The purified proteins are substantially free from other proteins with which they are co-produced as well as from other contaminants. Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620-625 (1981), or alternatively, Kaufman et al, *Mol. Cell. Biol.*, 5(7):1750-1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis,* Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering,* 8:277-298 (Plenum Press 1986) and references cited therein.

Another aspect of the present invention provides vectors for use in expression of these novel BMP-2 and BMP-4 polypeptides. Preferably the vectors contain the full novel DNA sequences described above which encode the novel factors of the invention. Additionally the vectors also contain appropriate expression control sequences permitting expression of the BMP-2 and BMP-4 protein sequences. Alternatively, vectors incorporating modified sequences as described above are also embodiments of the present invention and useful in the production of the BMP-2 and BMP-4 proteins. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to one of skill in the art and may be selected depending upon the selected host cells. Such selection is routine and does not form part of the present invention.

A protein of the present invention, which induces cartilage and/or bone growth in circumstances where bone is not normally formed, has application in the healing of bone fractures and cartilage defects in humans and other animals. Such a preparation employing a BMP-2 or BMP-4 protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-2 or BMP-4 protein may be used in the treatment of periodontal disease, and in other tooth repair processes. Such agents may provide an environment to attract bone-forming cells, stimulate growth of bone-forming cells or induce differentiation of progenitors of bone-forming cells. BMP-2 and BMP-4 polypeptides of the invention may also be useful in the treatment of osteoporosis. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair).

The proteins of the invention may increase neuronal survival and therefore be useful in transplantation and treatment of conditions exhibiting a decrease in neuronal survival.

A further aspect of the invention is a therapeutic method and composition for repairing fractures and other conditions related to cartilage and/or bone defects or periodontal diseases. In addition, the invention comprises therapeutic methods and compositions for wound healing and tissue repair. Such compositions comprise a therapeutically effective amount of a BMP-2 or BMP-4 protein of the invention in admixture with a pharmaceutically acceptable vehicle, carrier or matrix.

It is expected that the proteins of the invention may act in concert with or perhaps synergistically with other related proteins and growth factors. Further therapeutic methods and compositions of the invention therefore comprise a therapeutic amount of a BMP-2 or BMP-4 protein of the invention with a therapeutic amount of at least one of the other BMP proteins disclosed in co-owned and concurrently filed U.S. applications described above. Such combinations may comprise separate molecules of the BMP proteins or heteromolecules comprised of different BMP moieties. For example, a BMP-2 or BMP-4 subunit may be linked to a BMP-1, BMP-3, BMP-5, BMP-6, BMP-7 or BMP-8 subunit. Such linkage may comprise disulfide bonds. A method and composition of the invention may comprise a disulfide linked dimer comprising a BMP-2 or BMP-4 protein subunit and another "BMP" protein subunit described above. One may comprise a heterodimer of BMP-2 and BMP-4 moieties. Another embodiment may comprise a heterodimer of BMP-2 and BMP-7 subunits.

In further compositions, BMP-2 and BMP-4 proteins may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-a and TGF-b), and insulin-like growth factor (IGF). The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP proteins. Particularly domestic animals and thoroughbred horses in addition to humans are desired patients for such treatment with BMP-2 and BMP-4 of the present invention.

BMP-2 may be used individually in a pharmaceutical composition. BMP-2 may also be used in combination with BMP-4 and/or one or more of the other BMP proteins disclosed in co-owned and co-pending U.S. applications as discussed above. BMP-4 may be used individually in pharmaceutical composition. In addition, it may be used in combination with other BMP proteins as described above.

The therapeutic method includes administering the composition topically, systematically, or locally as an implant or device. When administered the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the BMP-2 and BMP-4 proteins which may also optionally be included in the composition as described above, may alternatively or additionally, be administered simultaneously or sequentially with the BMP composition in the methods of the invention. Preferably for bone and/or cartilage formation, the composition would include a matrix capable of delivering BMP-2, BMP-4 or other BMP proteins to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the BMP-2 and BMP-4 compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-2 and BMP-4 proteins, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the types of BMP proteins in the composition. The addition of other known growth factors, such as IGF I (insulin like growth factor I), to the final composition, may also effect the dosage. Progress can be monitored by periodic assessment of bone growth and/or repair, for example, x-rays, histomorphometric determinations and tetracycline labeling.

The following examples illustrate practice of the present invention in recovering and characterizing bovine BMP-2 protein and employing it to recover the human proteins BMP-2 and BMP-4, and in expressing the proteins via recombinant techniques.

EXAMPLE I

Isolation of Bovine Bone Inductive Factor

Ground bovine bone powder (20-120 mesh, Helitrex) is prepared according to the procedures of M. R. Urist et al., *Proc. Natl Acad. Sci USA,* 70:3511 (1973) with elimination of some extraction steps as identified below. Ten kgs of the ground powder is demineralized in successive changes of 0.6N HCl at 4° C. over a 48 hour period with vigorous stirring. The resulting suspension is extracted for 16 hours at 4° C. with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM. Tris (pH 7.4), 1 mM N-ethylmaleimide, 1 mM iodoacetamide, 1 mM phenylmethylsulfonyl fluorine as described in *Clin. Orthop. Rel. Res.,* 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1M NaCl, 6M urea (pH 7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath-Reddi assay (described in Example III below) desorbed from the column by 50 mM NaAc, 0.25 mM NaCl, 6M urea (pH 4.6). The protein from this step elution is concentrated 20- to 40-fold, then diluted 5 times with 80 mM $KPO_4$, 6M urea (pH 6.0). The pH of the solution is adjusted to 6.0 with 500 mM $K_2HP0_4$. The sample is applied to an hydroxylapatite column (LKB) equilibrated in 80 mM $KPO_4$, 6M urea (pH 6.0) and all unbound protein is removed by washing the column with the same buffer. Protein having bone and/or cartilage formation activity is eluted with 100 mM $KPO_4$ (pH 7.4) and 6M urea.

The protein is concentrated approximately 10 times, and solid NaCl added to a final concentration of 0.15M. This material is applied to a heparin—Sepharose column equilibrated in 50 mM KPO$_4$, 150 mM NaCl, 6M urea (pH 7.4). After extensive washing of the column with starting buffer, a protein with bone and/or cartilage inductive activity is eluted by 50 mM KPO$_4$, 700 mM NaCl, 6M urea (pH 7.4). This fraction is concentrated to a minimum volume, and 0.4 ml aliquots are applied to Superose 6 and Superose 12 columns connected in series, equilibrated with 4M GuCl, 20 mM Tris (pH 7.2) and the columns developed at a flow rate of 0.25 ml/min. The protein demonstrating bone and/or cartilage inductive activity has a relative migration on SDS-PAGE corresponding to approximately 30,000 dalton protein.

The above fractions from the superose columns are pooled, dialyzed against 50 mM NaAc, 6M urea (pH 4.6), and applied to a Pharmacia MonoS HR column. The column is developed with a gradient to 1.0M NaCl, 50 mM NaAc, 6M urea (pH 4.6). Active bone and/or cartilage formation fractions are pooled and brought to pH 3.0 with 10% trifluoroacetic acid (TFA). The material is applied to a 0.46×25 cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active material is eluted at approximately 40-44% acetonitrile. Aliquots of the appropriate active fractions are iodinated by one of the following methods: P. J. McConahey et al, *Int. Arch. Allergy*, 29:185-189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis and urea Triton X100 isoelectric focusing. At this stage, the protein having bone and/or cartilage forming activity is estimated to be approximately 10-50% pure.

EXAMPLE II

Characterization of Bovine Bone Inductive Factor

A. Molecular Weight

Approximately 20 ug protein from Example I is lyophilized and redissolved in 1× SDS sample buffer. After 15 minutes of heating at 37° C., the sample is applied to a 15% SDS polyacrylamide gel and then electrophoresed with cooling. The molecular weight is determined relative to prestained molecular weight standards (Bethesda Research Labs). Immediately after completion, the gel lane containing bone and/or cartilage forming material is sliced,into 0.3 cm pieces. Each piece is mashed and 1.4 ml of 0.1% SDS is added. The samples are shaken gently overnight at room temperature to elute the protein. Each gel slice is desalted to prevent interference in the biological assay. The supernatant from each sample is acidified to pH 3.0 with 10% TFA, filtered through a 0.45 micron membrane and loaded on a 0.46 cm×5 cm C4 Vydac column developed with a gradient of 0.1% TFA to 0.1% TFA, 90% CH$_3$CN. The appropriate bone and/or cartilage inductive protein-containing fractions are pooled and reconstituted with 20 mg rat matrix and assayed. In this gel system, the majority of bone and/or cartilage inductive fractions have the mobility of a protein having a molecular weight of approximately 28,000-30,000 daltons.

B. Isoelectric Focusing

The isoelectric point of bone inductive factor activity is determined in a denaturing isoelectric focusing system. The Triton X100 urea gel system, (Hoeffer Scientific) is modified as follows: 1) 40% of the ampholytes used are Servalyte 3/10; 60% are Servalyte 7-9; and 2) the catholyte used is 40 mM NaOH. Approximately 20 ug of protein from Example I is lyophilized, dissolved in sample buffer and applied to the isoelectrofocusing gel. The gel is run at 20 watts, 10 C. for approximately 3 hours. At completion the lane containing bone and/or cartilage inductive factor is sliced into 0.5 cm slices. Each piece is mashed in 1.0 ml 6M urea, 5 mM Tris (pH 7.8) and the samples agitated at room temperature. The samples are acidified, filtered, desalted and assayed as described above. The major portion of activity as determined by the Rosen-modified Sampath-Reddi assay migrates in a manner consistent with a pI of about 8.8-9.2.

C. Subunit Characterization

The subunit composition of the isolated bovine bone protein is also determined. Pure bone inductive factor is isolated from a preparative 15% SDS gel as described above. A portion of the sample is then reduced with 5 mM DTT in sample buffer and re-electrophoresed on a 15% SDS gel. The approximately 28-30 kd protein yields two major bands at approximately 18-20 kd and approximately 16-18 kd, as well as a minor band at approximately 28-30 kd. The broadness of the two bands indicates heterogeneity caused most probably by glycosylation, other post translational modification, proteolytic degradation or carbamylation.

EXAMPLE III

Rosen Modified Sampath-Reddi Assay

A modified version of the rat bone formation assay described in Sampath and Reddi, *Proc. Natl. Acad. Sci. U.S.A.*, 80:6591-6595 (1983) is used to evaluate bone and/or cartilage activity of the bovine protein obtained in Example I and the BMP-2 proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21-49 day old male Long Evans rats. The implants are removed after 7-14 days. Half of each implant is used for alkaline phosphatase analysis [See, A. H. Reddi et al., *Proc. Natl Acad Sci.*, 69:1601 (1972)].

The other half of each implant is fixed and processed for histological analysis. 1 μm glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone.

The rat matrix samples containing at least 200 ng of bovine protein obtained in Example I result in bone and/or cartilage formation that filled more than 20% of the implant areas sectioned for histology. This protein therefore scores at least +2 in the Rosen-modified Sampath-Reddi assay. The dose response of the matrix samples indicates that the amount of bone and/or cartilage formed increases with the amount of protein in the sample. The control sample did not result in any bone and/or cartilage formation. The purity of the protein assayed is approximately 10-15% pure.

The bone and/or cartilage formed is physically confined to the space occupied by the matrix. Samples are also analyzed by SDS gel electrophoresis and isoelectric focusing as described above, followed by autoradiography. Analysis reveals a correlation of activity with protein bands at 28-30 kd and a pI of approximately 8.8-9.2. To estimate the purity of the protein in a particular fraction an extinction coefficient of 1 OD/mg-cm is used as an estimate for protein and the protein is run on SDS PAGE followed by silver staining or radioiodination and autoradiography.

EXAMPLE IV

Bovine BMP-2

The protein composition of Example IIA of molecular weight 28-30 kd is reduced as described in Example IIC and digested with trypsin. Eight tryptic fragments are isolated by standard procedures having the following amino acid sequences:

```
Fragment 1: A A F L G D I A L D E E D L G

Fragment 2: A F Q V Q Q A A D L

Fragment 3: N Y Q D M V V E G

Fragment 4: S T P A Q D V S R

Fragment 5: N Q E A L R

Fragment 6: L S E P D P S H T L E E

Fragment 7: F D A Y Y

Fragment 8: L K P S N ? A T I Q S I V E
```

Two probes consisting of pools of oligonucleotides (or unique oligonucleotides) are designed according to the method of R. Lathe, *J. Mol. Biol.*, 183(1):1-12 (1985) on the basis of the amino acid sequence of Fragment 3 and synthesized on an automated DNA synthesizer as described above.

```
Probe #1: A C N A C C A T [A/G] T C [T/C] T G [A/G]
          A T

Probe #2: C A [A/G] G A [T/C] A T G G T N G T N G A
```

Because the genetic code is degenerate (more than one codon can code for the same amino acid), the number of oligonucleotides in a probe pool is reduced based on the frequency of codon usage in eukaryotes, the relative stability of G:T base pairs, and the relative infrequency of the dinucleotide CpG in eukaryotic coding sequences [See J. J. Toole et al, *Nature*, 312:342-347 (1984)]. Bracketed nucleotides are alternatives. "N" means either A, T, C or G. These probes are radioactively labeled and employed to screen a bovine genomic library. The library is constructed as follows: Bovine liver DNA is partially digested with the restriction endonuclease enzyme Sau 3A and sedimented through a sucrose gradient. Size fractionated DNA in the range of 15-30 kb is then ligated to the vector lambda J' Bam H1 arms [Mullins et al., *Nature*, 308:856-858 (1984)]. The library is plated at 8000 recombinants per plate. Duplicate nitrocellulose replicas of the plaques are made and amplified according to a modification of the procedure of Woo et al, *Proc. Natl. Acad. Sci. USA*, 75:3688-91 (1978). Probe #1 is hybridized to the set of filters in 3M tetramethylammonium chloride (TMAC), 0.1M sodium phosphate pH 6.5, 1 mM EDTA, 5× Denhardts, 0.6% SDS, 100 ug/ml salmon sperm DNA at 48 degrees C., and washed in 3M TMAC, 50 mM Tris pH 8.0 at 50 degrees C. These conditions minimize the detection of mismatches to the 17 mer probe pool [see, Wood et al, *Proc. Natl. Acad. Sci, U.S.A.*, 82:1585-1588 (1985)].

400,000 recombinants are screened by this procedure. One duplicate positive is plaque purified and the DNA is isolated from a plate lysate of the recombinant bacteriophage designated lambda bP-21. Bacteriophage bP-21 was deposited with the American Type Culture Collection, 12301 Parklawn Drive, Rockville, Md. USA (hereinafter the "ATCC") under accession number ATCC 40310 on Mar. 6, 1987. This deposit as well as the other deposits contained herein meets the requirements of the Budapest Treaty on the International Recognition of the Deposit of Microorganisms for the Purposes of Patent Procedure and Regulations thereunder. The bP-21 clone encodes at least a portion of a bovine BMP-2 protein designated bovine BMP-2 or bBMP-2.

The oligonucleotide hybridizing region of this BMP-2 clone is localized to an approximately 1.2 kb Sac I restriction fragment which is subcloned into M13 and sequenced by standard techniques. The partial DNA sequence and derived amino acid sequence of this Sac I fragment and the contiguous Hind III-Sac I restriction fragment of bP-21 are shown below in FIG. 1 (SEQ ID NO: 1). The BMP-2 peptide sequence from this clone is 129 amino acids in length and is encoded by the DNA sequence from nucleotide #1 through nucleotide #387 (SEQ ID NO: 1). The amino acid sequence corresponding to the tryptic fragment isolated from the bovine bone 28 to 30 kd material is underlined in FIG. 1. The underlined portion of the sequence corresponds to tryptic Fragment 3 above from which the oligonucleotide probes for BMP-2 are designed. The predicted amino acid sequence indicates that tryptic Fragment 3 is preceded by a basic residue (K) as expected considering the specificity of trypsin. The arginine residue encoded by the CGT triplet is presumed to be the carboxy-terminus of the protein based on the presence of a stop codon (TAG) adjacent to it.

EXAMPLE V

Human BMP-2 and BMP-4

The HindIII-SacI bovine genomic BMP-2 fragment described in Example IV is subcloned into an M13 vector. A $^{32}$P-labeled single-stranded DNA probe is made from a template preparation of this subclone. This probe is used to screen polyadenylated RNAs from various cell and tissue sources. Polyadenylated RNAs from various cell and tissue sources are electrophoresed on formaldehyde-agarose gels and transferred to nitrocellulose by the method of Toole et al., supra. The probe is then hybridized to the nitrocellulose blot in 50% formamide, 5× SSC, 0.1% SDS, 40 mM sodium phosphate pH 6.5, 100 ug/ml denatured salmon sperm DNA, and 5 mM vanadyl ribonucleosides at 42° C. overnight and washed at 65° C. in 0.2× SSC, 0.1% SDS. A hybridizing band corresponding to an mRNA species of approximately 3.8 kb is detected in the lane containing RNA from the human osteosarcoma cell line U-2 OS. cDNA is synthesized from U-2 OS polyadenylated RNA and cloned into lambda GT10 by established. techniques (Toole et al, supra). 20,000 recombinants from this library are plated on each of 50 plates. Duplicate nitrocellolose replicas are made of the plates.

The HindIII-SacI fragment is labeled with $^{32}$P by nick translation and used to screen the nitrocellulose filter replicas of the above-described U-2 OS cDNA library by hybridization in standard hybridization buffer at 65° overnight followed by washing in 1× SSC, 0.1% SDS at 65°. Twelve duplicate positive clones are picked and replated for secondaries. Duplicate nitrocellulose replicas are made of the secondary plates and both sets hybridized to the bovine genomic probe as the primary screening was performed. One set of filters is then washed in 1× SSC, 0.1% SDS; the other in 0.1× SSC, 0.1% SDS at 65°.

Two classes of hBMP-2 cDNA clones are evident based on strong (4 recombinants) or weak (7 recombinants) hybridization signals under the more stringent washing conditions (0.1× SSC, 0.1% SDS). All 11 recombinant bacteriophage are plaque purified, small scale DNA preparations made from plate lysates of each, and the inserts subcloned into pSP65 and into M13 for sequence analysis. Sequence analysis of the strongly hybridizing clones designated hBMP-2 (previously designated BMP-2A and BMP-2 Class I) indicates that they have extensive sequence homology with the sequence given in FIG. 1 (SEQ ID NO: 1). These clones are therefore cDNA encoding the human equivalent of the protein encoded by the bBMP-2 gene whose partial sequence is given in FIG. 1. Sequence analysis of the weakly hybridizing recombinants designated hBMP-4 (previously designated BMP-2B and BMP-2 Class II) indicates that they are also quite homologous with the sequence given in FIG. 1 (SEQ ID NO: 1) at the 3' end of their coding regions, but less so in the more 5' regions. Thus they encode a human protein of similar, though not identical, structure to that above.

Full length human BMP-2 cDNA clones are obtained in the following manner. The 1.5 kb insert of one of the BMP-4 subclones (II-10-1) is isolated and radioactively labeled by nick-translation. One set of the nitrocellulose replicas of the U-2 OS cDNA library screened above (50 filters, corresponding to 1,000,000 recombinant bacteriophage) are rehybridized with this probe under stringent conditions (hybridization at 65° in standard hybridization buffer; washing at 65° in 0.2× SSC, 0.1% SDS). All recombinants which hybridize to the bovine genomic probe which do not hybridize to the BMP-4 probe are picked and plaque purified (10 recombinants). Plate stocks are made and small scale bacteriophage DNA preparations made. After subcloning into M13, sequence analysis indicates that 4 of these represent clones which overlap the original BMP-2 clone. One of these, lambda U2OS-39, contains an approximately 1.5 kb insert and was deposited with the ATCC on Jun. 16, 1987 under accession number 40345. The DNA sequence (SEQ ID NO: 3) (compiled from lambda U20S-39 and several other hBMP-2 cDNA recombinants) and derived amino acid sequence (SEQ ID NO: 4) are shown below in FIG. 2. Lambda U2OS-39 is expected to contain all of the nucleotide sequence necessary to encode the entire human counterpart of the protein BMP-2 encoded by the bovine gene segment whose partial sequence is presented in FIG. 1. The BMP-2 protein encoded by the DNA sequence of FIG. 2 is contemplated to contain the 97 amino acid sequence from amino acid #299 to #396 or a sequence substantially homologous thereto. This human cDNA hBMP-2 contains an open reading frame of 1188 bp, encoding a protein of 396 amino acids. The protein is preceded by a 5' untranslated region of 342 bp with stop codons in all frames. The 13 bp region preceding this 5' untranslated region represents a linker used in the cDNA cloning procedure. This protein of 396 amino acids has a molecular weight of 45 kd based on this amino acid sequence. It is contemplated that this sequence represents the primary translation product. It is further contemplated that BMP-2 may correspond to the approximately 18-20 kd subunit of Example IIC. The sequence corresponding to the sequence tryptic Fragment 3 of Example IV is underlined in FIG. 2. The "pre" portion of the human BMP-2 protein is contemplated to comprise amino acid #1 to amino acid #23 as shown in FIG. 2. The "pro" portion is contemplated to comprise amino acid #24 to amino acid #282 of FIG. 2 (SEQ ID NO: 4). The mature portion is contemplated to comprise amino acid #283 (Gln, Ala, Lys . . . ) to #396 (Arg) of FIG. 2.

BMP-2 proteins of the invention comprise at least the amino acid sequence from amino acid #299 to #396, although further included in the invention are protein species with a carboxy terminus which is characterized by an amino acid upstream from amino acid #396.

Full-length BMP-4 human cDNA clones are obtained in the following manner. The 200 bp EcoRI-SacI fragment from the 5' end of the BMP-4 recombinant II-10-1 is isolated from its plasmid subclone, labeled by nick-translation, and hybridized to a set of duplicate nitrocellulose replicas of the U-2 OS cDNA library (25 filters/set; representing 500,000 recombinants). Hybridization and washing are performed under stringent conditions as described above. 16 duplicate positives are picked and replated for secondaries. Nitrocellulose filter replicas of the secondary plates are made and hybridized to an oligonucleotide which was synthesized to correspond to the sequence of II-10-1 and is of the following sequence:

CGGGCGCTCAGGATACTCAAGACCAGTGCTG

Hybridization is in standard hybridization buffer AT 50° C. with washing at 50° in 1× SSC, 0.1% SDS. 14 recombinant bacteriophage which hybridize to this oligonucleotide are plaque purified. Plate stocks are made and small scale bacteriophage DNA preparations made. After suclonIng 3 of these into M13, sequence analysis indicates that they represent clones which overlap the original BMP-4 clone. One of these, lambda U2OS-3, was deposited with the ATCC under accession number 40342 on Jun. 16, 1987. U2OS-3 contains an insert of approximately 1.8 kb. The DNA sequence (SEQ ID NO: 5) and derived amino acid sequence (SEQ ID NO: 6) of U2OS-3 are shown below in FIG. 3. This clone is expected to contain all of the nucleotide sequence necessary to encode the entire human BMP-4 protein. The BMP-4 protein encoded by FIG. 3 is contemplated to contain the 97 amino acid sequence from amino acid #311 to #408 or a sequence substantially homologous thereto. This cDNA contains an open reading frame of 1224 bp, encoding a protein of 408 amino acids, preceded by a 5' untranslated region of 394 bp with stop codons in all frames, and contains a 3' untranslated region of 308 bp following the in-frame stop codon. The 8 bp region preceding the 5' untranslated region represents a linker used in the cDNA cloning procedure. This protein of 408 amino acids has molecular weight of 47 kd and is contemplated to represent the primary translation product. Mature BMP-4 is contemplated to comprise amino acid #293 (Ser, Pro, Lys . . . )—#408 (Arg) of FIG. 3. A sequence similar though not idential to tryptic Fragment 3 of Example IV is underlined in FIG. 3 (SEQ ID NO: 6). The underlined sequence Asn-Tyr-Gln-Glu-Met-Val-Val-Glu-Gly differs from the tryptic fragment Asn-Tyr-Gln-Asp-Met-Val-Val-Glu-Gly by one amino acid in position four.

The sequences of BMP-2 and BMP-4, as shown in FIGS. 2 and 3, have significant homology to the beta (B) and beta (A) subunits of the inhibins. The inhibins are a family of hormones which are presently being investigated for use in contraception. See, A. J. Mason et al, Nature, 318:659-663 (1985). To a lesser extent they are also homologous to Mullerian inhibiting substance (MIS), a testicular glycoprotein that causes regression of the Mullerian duct during development of the male embryo, and transforming growth factor-beta (TGF-β) which can inhibit or stimulate growth of cells or cause them to differentiate. Furthermore, the sequences of FIGS. 2 and 3 indicate that BMP-2 and BMP-4 have significant homology to the Drosophila decapentaplegic (DPP-C) locus transcript. See, J. Massague, Cell, 49:437-438 (1987); R. W. Padgett et al, Nature, 325:81-84 (1987); R. L. Cate et al, Cell 45: 685-698 (1986). It is considered possible therefore that a BMP-2 protein is the human homolog of the protein made from this transcript from this developmental mutant locus. BMP-2 and BMP-4 share sequence similarity with Vg1. Vg1 mRNA has been localized to the vegetal hemisphere of Xenopus oocytes. During early development, it is distributed throughout the endoderm, but the mRNA is not detectable after blastula formation has occurred. The Vg1 protein may be the signal used by the endoderm cells to commit ectodermal cells to become the embryonic mesoderm.

The procedures described above may be employed to isolate other related BMP-2 and BMP-4 proteins of interest by utilizing the bovine BMP-2 and BMP-4 proteins as a probe source. Such other BMP-2 and BMP-4 proteins may find similar utility in, inter alia, fracture repair, wound healing and tissue repair.

EXAMPLE VI

Expression of BMP-2 and BMP-4

In order to produce bovine, human or other mammalian BMP-2 and BMP-4 proteins, the DNA encoding the desired protein is transferred into an appropriate expression vector and introduced into mammalian cells or other preferred eukaryotic or prokaryotic hosts by conventional genetic engineering techniques. The presently preferred expression system for biologically active recombinant human BMP-2 and BMP-4 is stably transformed mammalian cells.

One skilled in the art can construct mammalian expression vectors by employing the sequence of FIGS. 1-3 (SEQ ID NO: 1, 3, and 5), or other DNA sequences containing the coding sequences of FIGS. 1-3, or other modified sequences and known vectors, such as pCD [Okayama et al., Mol. Cell Biol., 2:161-170 (1982)] and pJL3, pJL4 [Gough et al., EMBO J., 4:645-653 (1985)]. The BMP-2 and BMP-4 cDNA sequences can be modified by removing the non-coding nucleotides on the 5' and 3' ends of the coding region. The deleted non-coding nucleotides may or may not be replaced by other sequences known to be beneficial for expression. The transformation of these vectors into appropriate host cells can result in expression of BMP-2 or BMP-4 proteins.

One skilled in the art could manipulate the sequences of FIGS. 1-3 (SEQ ID NO: 1, 3, and 5) by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences there-from or altering nucleotides therein by other known techniques). The modified BMP-2 or BMP-4 coding sequence could then be inserted into a known bacterial vector using procedures such as described in T. Taniguchi et al., Proc. Natl Acad. Sci. USA, 77:5230-5233 (1980). This exemplary bacterial vector could then be transformed into bacterial host cells and BMP-2 protein or BMP-4 expressed thereby. For a strategy for producing extracellular expression of BMP-2 or BMP-4 proteins in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-2 or BMP-4 protein of the invention in mammalian cells involves the construction of cells containing multiple copies of the heterologous BMP-2 or BMP-4 gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, J. Mol. Biol., 159:601-629 (1982). This approach can be employed with a number of different cell types.

For example, a plasmid containing a DNA sequence for a BMP-2 or BMP-4 of the invention in operative association with other plasmid sequences enabling expression thereof and the DHFR expression plasmid pAdA26SV(A)3 [Kaufman and Sharp, Mol. Cell. Biol., 2:1304 (1982)] can be co-introduced into DHFR-deficient CHO cells, DUKX-BII, by calcium phosphate coprecipitation and transfection, electroperation, protoplast fusion or lipofection. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 uM MTX) as described in Kaufman et al., Mol Cell Biol., 5:1750 (1983).

Transformants are cloned, and biologically active BMP-2 or BMP-4 expression is monitored by the Rosen-modified Sampath-Reddi rat bone formation assay described above in Example III. BMP-2 and BMP-4 expression should increase with increasing levels of MTX resistance. Similar procedures can be followed to produce other related BMP-2 and BMP-4 proteins.

A. COS Cell Expression

As one specific example of producing a BMP-2 protein of the invention, the insert of II-3 (a λ GT10 derivative containing the full length BMP-2 cDNA) is released from the vector arms by digestion with EcoRI and subcloned into pSP65 (Promega Biotec, Madison, Wis.) [Melton et al, Nucl. Acids Res. 12:7035-7056 (1984)] in both orientations yielding pBMP-2 #39-3 or pBMP-2 #39-4. The insert is subcloned into the EcoRI site of the mammalian expression vector, pMT2 CXM, described below, though derivitives thereof may also be suitable. Plasmid DNA from this subclone is transfected into COS cells by the DEAE-dextran procedure (Sompayrac and Danna *PNAS* 78:7575-7578 (1981); Luthman and Magnusson, *Nucl. Acids Res.* 11: 1295-1308 (1983)] and the cells are cultured. Serum-free 24 hr. conditioned medium is collected from the cells starting 40-70 hr. post-transfection. Recovery and purification of the COS expressed BMP-2 proteins is described below in Example VII.

The mammalian expression vector pMT2 CXM is a derivative of p91023 (b) (Wong et al., Science 228:810-815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689-693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. pMT2 CXM is then constructed using loopout/in mutagenesis [Morinaga, et al., *Biotechnology* 84: 636 (1984). This removes bases 1075 to 1145 relative to the Hind III site near the SV40 origin of replication and enhancer sequences of pMT2. In addition it inserts the following sequence:

5' PO$_c$ATGGGCAGCTCGAG-3' at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

B. CHO Cell Expression (1) BMP-2 Expression in CHO Cells

In order to achieve high levels of human BMP-2 protein expression, the DNA sequence of FIG. 2 (SEQ ID NO: 3) encoding BMP-2 is inserted into a eucaryotic expression vector, stably introduced into CHO cells and amplified to high copy number by methotrexate selection of DHFR [R. J. Kaufman, et al., *EMBO J.* 6:189 (1987)]. The transformed cells are cultured and the expressed BMP-2 proteins are recovered and purified from the culture media.

A BMP-2 protein of the invention is expressed in CHO cells by releasing the insert of pBMP-2 #39-3 described above, from the vector by digestion with EcoRI. The insert is subcloned into the EcoRI cloning site of the mammalian expression vector, pMT2 CXM described above, though derivitives thereof may also be suitable.

A derivative of the BMP-2 cDNA sequence set forth in FIG. 2 (SEQ ID NO: 3) in which the 5' untranslated region is deleted is made by removal of the sequences contained between the SalI site at the 5' adapter (from the original cDNA cloning), and the SalI site 7 base pairs upstream of the initiator ATG, by digestion with SalI and religation. This step is conveniently performed in either SP65 derivatives containing the full length BMP-2 cDNA, but can also be performed in pMT2 derivatives. The 3' untranslated region is removed using heteroduplex mutagenesis using the mutagenic oligonucleotide 5' GAGGGTTGTGGGTGTCGC<u>TAGTGA</u><u>GTCGACT</u>ACAGCAAAATT
                                  Terminator  SalI The sequence contains the terminal 3' coding region of the BMP-2 cDNA, followed immediately by a recognition site for SalI.

The BMP-2 cDNA with deletions of the 5' and 3' untranslated regions are excised from pSP65 with SalI, and subcloned into the SalI site of pMT23 described above. Plasmid DNA from the subclones is transfected into CHO cells by electroporation [Neuman et al, *EMBO J.,* 1:841-845 (1982)]. Two days later, cells are switched to selective medium containing 10% dialyzed fetal bovine serum and lacking nucleosides. Colonies expressing DHFR are counted 10-14 days later. Individual colonies or pools of colonies are expanded and analyzed for expression of BMP-2 RNA and protein using standard procedures and are subsequently selected for amplification by growth in increasing concentrations of MTX. Stepwise selection of the preferred pool, termed 2ΔD, is carried out up to a concentration of 2 μM MTX. Individual cells from the pool are then cloned and assayed for BMP-2 expression. Procedures for such assay include Northern Blot analysis to detect the presence of RNA, protein analysis including SDS-PAGE and analysis for cartilage and/or bone formation activity using the ectopic rat bone formation assay described above. The presently preferred clonally-derived cell line is identified as 2ΔD2I. This cell line secretes BMP-2 proteins into the media containing 2 μM MTX.

The CHO cell line 2ΔD2I is grown in Dulbecco's modified Eagle's medium (DMEM)/Ham's nutrient mixture F-12, 1:1 (vol/vol), supplemented with 10% fetal bovine serum. When the cells are 80-100% confluent, the medium is replaced with serum-free DMEM/F-12. Medium is harvested every 24 hours for 4 days. For protein production and purification the cells are cultured serum-free.

Currently, this cell line 2ΔD2I is being subjected to stepwise selection in increasing concentrations of MTX (10 μM, 100 μM, 1000 μM) which may potentially yield cells which produce even higher levels of BMP-2 protein expression.

cDNA genes inserted into the EcoRI and/or Xho I sites are expressed as a bicistronic mRNA with DHFR in the second position. In this configuration, translation of the upstream (BMP-2) open reading frame is more efficient than the downstream (DHFR) cDNA gene [Kaufman et al, *EMBO J.* 6:187-193 (1987). The amount of DHFR protein expressed is nevertheless sufficient for selection of stable CHO cell lines.

Characterization of the BMP-2 polypeptides through pulse labeling with [35S] methionine or cysteine and polyacrylamide gel electrophoresis indicates that multiple molecular size forms of BMP-2 proteins, further described below, are being expressed and secreted from the stable CHO lines.

(2) BMP-4 Expression in CHO Cells

In order to achieve high levels of human BMP-4 protein expression, the DNA sequence of FIG. 3 (SEQ ID NO: 5) encoding BMP-4 is inserted into a eucaryotic expression vector, stably introduced into CHO cells and amplified to high copy number by methotrexate selection of DHFR [R. J. Kaufman, et al., *EMBO J.* 6:189 (1987)]. The transformed cells are cultured and the expressed BMP-4 proteins are recovered and purified from the culture media.

As described above, numerous expression vectors known in the art may be utilized in the expression of BMP proteins of the invention. The vector utilized in the following example is pEMC2β1 derived from pMT21 though other vectors may be suitable in practice of the invention.

pMT21 is derived from $pMT_2$ which is derived from pMT2-VWF, deposited with the American Type Culture Collection (ATCC), Rockville, Md. (USA) under accession number ATCC 67122 under the provisions of the Budapest Treaty. EcoRI digestion excises the cDNA insert present in pMT-VWF, yielding pMT2 in linear form which can be ligated and used to transform *E. Coli* HB 101 or DH-5 to ampicillin resistance. Plasmid pMT2 DNA can be prepared by conventional methods.

pMT21 was derived from pMT2 through the following two modifications. First, 76 bp of the 5' untranslated region of the DHFR cDNA including a stretch of 19 G residues from G/C tailing for cDNA cloning was deleted. In this process, a XhoI site was inserted to obtain the following sequence immediately upstream from DHFR:

```
5'-CTGCAGGCGAGCCTGAATTCCTCGAGCCATCATG-3'
     PstI         Eco RI XhoI
```

Second, a unique ClaI site was introduced by digestion with EcoRV and XbaI, treatment with Klenow fragment of DNA polymerase I, and ligation to a ClaI linker (CATCGATG). This deletes a 250 bp segment from the adenovirus virus associated RNA (VAI) region but does not interfere with VAI RNA gene expression or function. pMT21 was digested with EcoRI and XhoI, and used to derive the vector pEMC2B1.

A portion of the EMCV leader was obtained from pMT2-ECAT1 [S. K. Jung, et al, *J. Virol* 63:1651-1660 (1989)] by digest with Eco RI and PstI, resulting in a 2752 bp fragment. This fragment was digested with TaqI yielding an Eco RI-TaqI fragment of 508 bp which was purified by electrophoresis on low melting agarose gel. A 68 bp adapter and its complementary strand were synthesized with a 5' TaqI protruding end and a 3' XhoI protruding end which has the following sequence:

```
5'-CGAGGTTAAAAAACGTCTAGGCCCCCCGAACCACGGGGACGTGGTTTT
   TaqI

CCTTTGAAAAACACGATTGC-3'
              XhoI
```

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulted in the vector pEMC2B1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the dadenovirus VA I gene, DHFR and B-lactamase markers and an EMC sequence, in appropriate relationships to direct the high level expression of the desired cDNA in mammalian cells.

A derivative of the BMP-4 cDNA sequence set forth in FIG. 3 in which the 3' untranslated region is removed is made via heteroduplex mutagenesis with the mutagenic oligonucleotide:

```
5' GGATGTGGGTGCCGCTGACTCTAGAGTCGACGGAATTC 3'.
                  Terminator         EcoRI
```

This deletes all of the sequences 3' to the translation terminator codon of the BMP-4 cDNA, juxtaposing this terminator codon and the vector polylinker sequences. This step is performed in an SP65 vector though may be conveniently performed in MT2 derivatives containing the BMP-4 cDNA. The 5' untranslated region is removed using the restriction endonuclease BsmI, which cleaves within the eighth codon of BMP-4 cDNA. Reconstruction of the first eight codons is accomplished by ligation to oliognucleotides:

```
     EcoRI  Initiator          BsmI
  5'  AATTCACCATGATTCCTGGTAACCGAATGCT 3' and

3'        GTGGTACTAAGGACCATTGGCTTAC    5'
```

These oligonucleotides form a duplex which has a BsmI complementary cohesive end capable of ligation to the BsmI restricted BMP-4 cDNA, and it has an EcoRI complementary cohesive end capable of ligation to the EcoRI restricted vector MT2. Thus the cDNA for BMP-4 with the 5' and 3' untranslated regions deleted, and retaining the entire encoding sequence is contained within an EcoRI restriction fragment of approximately 1.2 kb.

The BMP-4 containing plasmid designated pXMBMP-4DUT is digested with EcoRI in order to release the BMP-4 cDNA containing insert from the vector. This insert is subcloned into the EcoRI site of the mammalian expression vector pEMC2β1 described above. Plasmid DNA from the subclones is transfected into CHO cells by electroporation [Neuman et al, *EMBO J.*, 1:841-845 (1982)]. Two days later, cells are switched to selective medium containing 10% dialyzed fetal bovine serum and lacking nucleosides. Colonies expressing DHFR are counted 10-14 days later. Individual colonies or pools of colonies are expanded and analyzed for expression of BMP-4 RNA and protein using standard procedures and are subsequently selected for amplification by growth in increasing concentrations of MTX. Stepwise selection of the preferred pool, termed 4ΔED, is carried out up to a concentration of 2 μM MTX. Individual cells from the pool are then cloned and assayed for BMP-4 expression. Procedures for such assay include Northern Blot analysis to detect the presence of mRNA, protein analysis including SDS-PAGE and analysis for cartilage and/or bone formation activity using the ectopic rat bone formation assay described above.

4ΔED is grown in Dulbecco's modified Eagle's medium (DMEM)/Ham's nutrient mixture F-12, 1:1 (vol/vol), supplemented with 10% fetal bovine serum. When the cells are 80-100% confluent, the medium is replaced with serum-free DMEM/F-12. Medium is harvested every 24 hours for 4 days. For protein production and purification the cells are cultured serum-free.

cDNA genes inserted into the EcoRI and/or Xho I sites are expressed as a bicistronic mRNA with DHFR in the second position. In this configuration, translation of the upstream (BMP-4) open reading frame is more efficient than the downstream (DHFR) cDNA gene [Kaufman et al, *EMBO J.* 6:187-193 (1987). The amount of DHFR protein expressed is nevertheless sufficient for selection of stable CHO cell lines.

Characterization of the BMP-4 polypeptides through pulse labeling with [35S] methionine or cysteine and polyacrylamide gel electrophoresis indicates that multiple molecular size forms of BMP-4 proteins, further described below, are being expressed and secreted from the stable CHO lines.

EXAMPLE VII

Characterization and Biological Activity of Expressed BMP-2 and BMP-4

To measure the biological activity of the expressed BMP-2 and BMP-4 proteins obtained in Example VI above, the proteins are recovered from the cell culture and purified by isolating the BMP-2 and BMP-4 proteins from other proteinaceous materials with which they are co-produced as well as from other contaminants. The purified protein is assayed in accordance with the rat bone formation assay described in Example III using a modified scoring method described below.

A. COS Expressed Protein

The COS expressed material of Example VI may be partially purified on a Heparin Sepharose column. 4 ml of the collected post transfection conditioned medium supernatant from one 100 mm culture dish is concentrated approximately 10 fold by ultrafiltration on a YM 10 membrane and then dialyzed against 20 mM Tris, 0.15 M NaCl, pH 7.4 (starting buffer). This material is then applied to a 1.1 ml Heparin Sepharose column in starting buffer. Unbound proteins are removed by an 8 ml wash of starting buffer, and bound proteins, including BMP-2 polypeptides, are desorbed by a 3-4 ml wash of 20 mM Tris, 2.0 M NaCl, pH 7.4.

The proteins bound by the Heparin column are concentrated approximately 10-fold on a Centricon 10 and the salt reduced by diafiltration with 0.1% trifluoroacetic acid. The appropriate amount of this solution is mixed with 20 mg of rat matrix and then assayed for in vivo bone and/or cartilage formation activity by the Rosen-modified Sampath-Reddi assay. A mock transfection supernatant fractionation is used as a control.

The implants containing rat matrix to which specific amounts of human BMP-2 or BMP-4 have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Addition of the expressed human BMP-2 or BMP-4 to the matrix material results in formation of cartilage-like nodules at 7 days post implantation. The chondroblast-type cells are recognizable by shape and expression of metachromatic matrix. The amount of activity observed for human BMP-2 or BMP-4 indicates that it may be dependent upon the amount of human BMP-2 or BMP-4 protein added to the matrix sample.

Similar levels of activity are seen in the Heparin Sepharose fractionated COS cell extracts. Partial purification is accomplished in a similar manner as described above except that 6 M urea is included in all the buffers.

B. CHO Expressed Protein (1) BMP-2

To measure the biological activity of the BMP-2 proteins expressed in accordance with Example VIB above, 0.5 liters of conditioned media is directly adsorbed to 1 ml Heparin Sepharose (Pharmacia) column. The resin is washed with 0.15 M NaCl, 6.0 M urea, 20 mM Tris, pH 7.4 and then developed with a linear gradient to 1.0 M NaCl, 6.0 M urea, 50 mM Tris, pH 7.4. Fractions are assayed by the rat ectopic cartilage and bone formation assay described in Example III. The highest specific activity fractions are pooled and concentrated by ultrafiltration on a YM-10 (Amicon) membrane. Conditioned medium from CHO cells not transfected with the BMP-2 gene is prepared similarly, except that a step gradient to 1 M NaCl is used. Protein concentration is determined by amino acid analysis.

Further purification is achieved by preparative NaDodSO$_4$/PAGE [Laemmli, *Nature* 227: 680-685 (1970)]. Approximately 300 µg of protein is applied to a 1.5-mm-thick 12.5% gel: recovery is estimated by adding L-[$^{35}$S] methionine-labeled BMP-2 purified over heparin-Sepharose as described above. Protein is visualized by copper staining of an adjacent lane [Lee, et al., *Anal. Biochem.* 166:308-312 (1987)]. Appropriate bands are excises and extracted in 0.1% NaDodSO$_4$/20 mM Tris, pH 8.0. The supernatant is acidified with 10% CF$_3$COOH to pH 3 and the proteins are desalted on 5.0×0.46 cm Vydac C$_4$ column (The Separations Group, Hesperia, Calif.) developed with a gradient of 0.1% CF$_3$COOH to 90% acetonitrile/0.1% CF$_3$COOH.

The pooled material is analyzed by SDS-PAGE using a 12% acrylamide (U. K. Laemmli, *Nature* 227:680 (1970)] stained with silver [R. R. Oakley, et al. *Anal. Biochem.* 105:361 (1980)] and by immunoblot [H. Towbin, et al. *Proc. Natl. Acad. Sci. USA* 76:4350 (1979)] of 13.5% gel. SDS-PAGE reveals that multiple molecular size forms of BMP-2 proteins are being expressed and secreted from the stable CHO lines. Under non-reduced conditions, the major protein species is represented by a broad band at 30,000 daltons. Lower molecular weight species are seen as well as higher species, most notably 82,000 daltons and 113,000 daltons.

The 30,000 dalton band reacts with a rabbit antiserum directed against an *E. coli* produced fragment of BMP-2 amino acids #130-#396 as shown in FIG. 2 (SEQ ID NO: 4), with which it was incubated followed by $^{125}$I-Protein A. Under reduced conditions the 30,000 dalton material shifts to the 16,000-20,000 range with several species within this range observed. Each band is recognized by a turkey-derived anti-peptide antibody directed against amino acids #350-#365 as shown in FIG. 2 with which it is incubated followed by $^{125}$I-rabbit anti-turkey IgG, as well as the anti-BMP-2 antibody described above. The peptide antibody is generated by coupling to bovine serum albumin with glutaraldehyde [J. P. Briand, et al. *J. Immunol. Meth.* 78:59 (1985)] in the presence of 100 ug/ml albumin. The broadness of the 30,000 dalton band and the mutiplicity of its subunits are contemplated to arise from differences in carbohydrate in the potential N-gylcosylation site or from N-terminal heterogeneity.

A major N-terminal amino acid sequence beginning at amino acid #283 (Gln, Ala, Lys . . . ) as shown in FIG. 2 is obtained from the 30,000 dalton band isolated under non-reducing conditions. The calculated subunit molecular weight of a protein of amino acids 283-396 is approximately 13,000 daltons. Preliminary experiments indicate that over 90% of the biological activity in the total protein pool is eluted from a non-reduced SDS-PAGE at a relative mass of 30,000 daltons. It is contemplated therefore that a dimer of amino acids #283-396 of BMP-2, (referred to as a mature BMP-2) accounts for the majority of the biological activity in the mixture of expressed BMP-2 proteins. It is further contemplated that processing of BMP-2 to the mature forms involves dimerization of the proprotein (amino acids #24 Leu, Val, Pro . . . to #396) and removal of the N-terminal region in a manner analogous to the processing of the related protein TGF-β [L. E. Gentry, et al. *Molec. & Cell Biol.* 8:4162 (1988); R. Dernyck, et al. *Nature* 316:701 (1985)].

Immunoblot analysis using antibodies directed against a portion of the mature region (amino acids #350-365) and an antibody directed against the pro region (amino acids #103-116) of the 82,000 and 113,000 higher molecular weight species of BMP-2 under both non-reduced and reduced conditions suggests that these species may represent intermediate forms in the processing of the BMP-2 dimer. A 66,000 dalton species is present under reduced conditions. The 113,000 dalton species is contemplated to comprise proprotein dimers of 113,000 daltons (2 subunits of 66,000 daltons) and the 82,000 dalton species is contemplated to comprise a proprotein subunit linked to a mature BMP-2 subunit (66,000 daltons plus 18,000 daltons). Based on these analyses, approximately 50% of the total protein is active mature BMP-2.

The pool of protein containing recombinant human BMP-2 is assayed in accordance with the rat cartilage and bone formation assay described in Example III using a modified scoring method as follows, three non-adjacent sections are evaluated from each implant and averaged. "+/−" indicates tentative identification of cartilage or bone; "+1" indicates >10% of each section being new cartilage or bone; "+2", >25%; "+3", >50%; "+4", −75%; "+5", >80%. A "−" indicates that the implant is not recovered. The scores of the individual implants (in triplicate) are tabulated to indicate assay variability. BMP-2 protein is implanted subcutaneously in rats for times ranging from 5-21 days and the resulting implants evaluated histologically for the presence of newly formed cartilage and bone. Additionally, the level of alkaline phosphatase, synthesized by both cartilage and bone cells is measured.

Addition of partially purified CHO expressed human BMP-2 to the matrix material induces both new cartilage and new bone formation. Implantation of amounts of 0.46-115.3 μg of protein tested for times ranging from 5-21 days results in the induction of new cartilage and bone formation. Induction of cartilage formation is evident by day 7 and induction of bone formation is evident by day 14 for the lowest dose. The time at which bone formation occurs is related to the amount of BMP-2 implanted. At high doses bone can be observed at five days.

The development of cartilage and bone with time of a 12.0 microgram dosage of protein containing BMP-2 is summarized below. Amounts of new cartilage and bone are evaluated semi-quantitatively and scored on a scale of 0 to 5. Individual implants are listed to illustrate assay variability. At 5 days, many immature and some hypertrophic cartilage cells are present in the BMP-containing implant, but no mineralizing cartilage is detected. After 7 days chondrogenesis progresses so that most of the cartilage cells are hypertrophic and surrounded by mineralized matrix. Osteoblasts appear to be actively secreting osteoid, which is not yet mineralized. Day 7 implants have the greatest alkaline phosphatase content reflecting production by both chondrocytes and osteoblasts. Vascular elements, including giant cells and bone marrow precursors, are seen and are most abundant in areas where calcified cartilage is undergoing remodeling.

The decline of alkaline phosphatase activity on day 10 signals the end of chondrogenesis in the implants. At 14 days the removal of calcified cartilage is nearly complete and bone is widespread. Osteoblasts and osteoclasts are abundant and appear to be actively engaged in the organization of newly formed trabecular bone. The levels of alkaline phosphatase reflect osteoblast activity at this stage in the maturation process. The vascularity of the implants has increased markedly, and hematopoietic cell maturation is tentatively observed.

At 21 days, implants show increased maturity over the previous time point. The bone is highly organized with mature marrow spaces, and bone-forming cells embedded in mineralized bone matrix are apparent. At 21 days, all remnants of matrix carrier have been removed in contrast to the control implants with no BMP, where matrix remains intact.

NaDodSO$_4$/PAGE is used to purify each of the three BMP-2 species to homogeneity. The overall recovery of BMP-2 protein after electrophoresis, desalting, and concentration is approximately 30% and 87% of the BMP-2 is the 30,000 dalton form. All three forms of BMP-2 show in vivo activity when assayed for cartilage and bone induction. The 30,000 and 82,000 dalton species were equivalent in this assay while the 113,000 dalton species showed significantly less activity.

(2) BMP-4

To measure the biological activity of BMP-4 expressed in accordance with Example VIB above BMP-4 is collected from the conditioned medium by batch adsorbing BMP-4 to heparin sepharose CL-6-B using swelled heparin sepharose per liter conditioned media (CM) and stirring overnight at 4° C. The heparin sepharose is collected by filtering the CM through a fitted glass filter and washed with cold (4° C.) 50 mM Tris pH 7.4. A Pharmacia column is packed with the heparin sepharose using 50 mM Tris buffer and washed with buffer to the baseline. Elution is carried out with the following gradient of sodium chloride:

Buffer A: 50 nM Tris pH 7.4
Buffer B: 50 nM Tris pH 7.4, 1M NaCl

BMP-4 containing fractions are located using Western blots probed with antipeptide antibody W10 (an anti-peptide polyclonal antibody recognizing the carboxy terminus of BMP-2). The BMP-4 containing fractions are pooled, the NaCl concentration is adjusted to 0.8M, and the pool is loaded onto a Butyl Toyopearl hydrophobic interaction column. Gradient elution from the hydrophobic interaction column is carried out using a sodium chloride and ethanol gradient:

Buffer A: 50 mM Tris pH 7,4, 0.8M NaCl
Buffer B: 50 mM Tris pH 7,4, 10% Ethanol

BMP-4 elutes at approximately 0.37M NaCl, 5.4% ethanol. The BMP-4 containing fractions are pooled and concentrated. Yields are approximately 33 μg/liter CM of >95% pure material.

SDS-PAGE and silver stain analysis reveals that BMP-4 typically migrates as a single band at approximately 35 kD (non-reduced) and reduces to a single bend at approximately 22 kD. BMP-4 is, therefore, a dimer of approximate molecular weight 35 kD which reduces to a monomer of approximate molecular weight 20 kD. Monomers of 18 and 22 kD have been detected. Monomer can also be seen reducing from a high molecular weight region (>67 kD) where it is assumed to be associated with an unprocessed BMP-4 molecule. The 2D pattern indicates that heterodimers are formed between the various molecular weight monomeric species.

BMP-4 is sensitive to N-glycanase, Endoglycosidase H, and Endoglycosidase F digestion, indicating the presence of N linked high mannose sugars. In a western format, ConA and WGA bind BMP-4, again indicating the presence of N-linked high mannose glycans. Lentil Lectin, which indicates the presence of α-D mannosyl or α-D glycosyl linkages, also binds BMP-4.

N-terminal sequence analysis reveals a single amino terminus at serine #293. Indicating a cleavage site at amino acid 293. This amino terminus is analogous to the Gln, Ala, Lys . . . of BMP-2. Mature BMP-4 is, therefore, a dimer of amino acids #293-#408 as shown in FIG. 3 (SEQ ID NO: 4).

Presently, experiments indicate a minimum dose of 156 ng reproducibly induces cartilage formation with BMP-4 in the rat ectopic assay which is comparable to BMP-2. Bone that is formed by BMP-4 is highly calcified, organized, and histologically similar to that formed by BMP-2, as described above. The time course of the appearance and the subsequent remodelling into bone is similar for BMP-4 and BMP-2.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A method for treating peridontal disease in a patient in need of same comprising administering a pharmaceutical composition comprising an effective amount of a BMP-2 protein in a pharmaceutically acceptable vehicle, wherein the BMP-2 protein is encoded by a nucleic acid that hybridizes under stringent hybridization conditions (hybridization at 65° C. in 6× SSC, 0.01M EDTA, 5× Denhardt's solution, 0.5% SDS, 100 μg/ml denatured salmon sperm DNA, labelled DNA probe; washing at 65° C. in 0.2× SSC, 0.1×SDS) to the complement of SEQ ID NO:1 or SEQ ID NO:3, wherein the encoded BMP protein has the ability to induce formation of cartilage or bone or both.

2. The method of claim 1, wherein the pharmaceutical composition further comprises collagen.

3. A method for treating peridontal disease in a patient in need of same comprising administering a pharmaceutical composition comprising an effective amount of a BMP-2 protein in a pharmaceutically acceptable vehicle, wherein the BMP-2 protein comprises the amino acid sequence of SEQ ID NO:2 or SEQ ID NO:4.

4. A method for treating peridontal disease in a patient in need of same comprising administering a pharmaceutical composition comprising an effective amount of a BMP-2 protein in a pharmaceutically acceptable vehicle, wherein the BMP-2 protein comprises amino acids 299–396 of SEQ ID NO:4.

5. A method for treating peridontal disease in a patient in need of same comprising administering a pharmaceutical composition comprising an effective amount of a BMP-2 protein in a pharmaceutically acceptable vehicle, wherein the BMP-2 protein comprises amino acids 32–129 of SEQ ID NO:2.

6. A method for treating peridontal disease in a patient in need of same comprising administering a pharmaceutical composition comprising an effective amount of a BMP-2 protein in a pharmaceutically acceptable vehicle, wherein the BMP-2 protein comprises the amino acid sequence encoded by the nucleic acid sequence of SEQ ID NO:1 or SEQ ID NO:3.

7. A method for treating peridontal disease in a patient in need of same comprising administering a pharmaceutical composition comprising an effective amount of a BMP-2 protein in a pharmaceutically acceptable vehicle, wherein the BMP-2 protein comprises the amino acid sequence encoded by nucleotides 1–387 of SEQ ID NO:1.

8. A method for treating peridontal disease in a patient in need of same comprising administering a pharmaceutical composition comprising an effective amount of a BMP-2 protein in a pharmaceutically acceptable vehicle, wherein the BMP-2 protein comprises the amino acid sequence encoded by nucleotides 356–1543 of SEQ ID NO:3.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 592 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: BOS TAURUS (vii) IMMEDIATE SOURCE:
      (A) LIBRARY: BOVINE GENOMIC IN LAMBDA J1
      (B) CLONE: LAMBDA BP-21

(viii) POSITION IN GENOME:
      (C) UNITS: bp (ix) FEATURE:
      (A) NAME/KEY: CDS
      (B) LOCATION: 1..390

(ix) FEATURE:
      (A) NAME/KEY: mat_peptide
      (B) LOCATION: 46..387

(xi) SEQUENCE DESCRIPTION: SEQ ID NO:1:

```
GGC CAC GAT GGG AAA GGA CAC CCT CTC CAC AGA AGA GAA AAG CGG CAA      48
Gly His Asp Gly Lys Gly His Pro Leu His Arg Arg Glu Lys Arg Gln
-15              -10                 -5                       1

GCA AAA CAC AAA CAG CGG AAA CGC CTC AAG TCC AGC TGT AAG AGA CAC      96
Ala Lys His Lys Gln Arg Lys Arg Leu Lys Ser Ser Cys Lys Arg His
              5                  10                  15

CCT TTA TAT GTG GAC TTC AGT GAT GTG GGG TGG AAT GAC TGG ATC GTT     144
Pro Leu Tyr Val Asp Phe Ser Asp Val Gly Trp Asn Asp Trp Ile Val
         20                  25                  30

GCA CCG CCG GGG TAT CAT GCC TTT TAC TGC CAT GGG GAG TGC CCT TTT     192
Ala Pro Pro Gly Tyr His Ala Phe Tyr Cys His Gly Glu Cys Pro Phe
         35                  40                  45
```

-continued

```
CCC CTG GCC GAT CAC CTT AAC TCC ACG AAT CAT GCC ATT GTC CAA ACT         240
Pro Leu Ala Asp His Leu Asn Ser Thr Asn His Ala Ile Val Gln Thr
 50              55                  60                  65

CTG GTC AAC TCA GTT AAC TCT AAG ATT CCC AAG GCA TGC TGT GTC CCA         288
Leu Val Asn Ser Val Asn Ser Lys Ile Pro Lys Ala Cys Cys Val Pro
             70                  75                  80

ACA GAG CTC AGC GCC ATC TCC ATG CTG TAC CTT GAT GAG AAT GAG AAG         336
Thr Glu Leu Ser Ala Ile Ser Met Leu Tyr Leu Asp Glu Asn Glu Lys
                 85                  90                  95

GTG GTA TTA AAG AAC TAT CAG GAC ATG GTT GTC GAG GGT TGT GGG TGT         384
Val Val Leu Lys Asn Tyr Gln Asp Met Val Val Glu Gly Cys Gly Cys
            100                 105                 110

CGT TAGCACAGCA AAATAAAATA TAAATATATA TATATATATA TTAGAAAAAC              437
Arg
    115

AGCAAAAAAA TCAAGTTGAC ACTTTAATAT TTCCCAATGA AGACTTTATT TATGGAATGG       497

AATGGAGAAA AAGAAAAACA CAGCTATTTT GAAAACTATA TTTATATCTA CCGAAAAGAA       557

GTTGGGAAAA CAAATATTTT AATCAGAGAA TTATT                                  592

(2) INFORMATION FOR SEQ ID NO:2:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:2:

Gly His Asp Gly Lys Gly His Pro Leu His Arg Arg Glu Lys Arg Gln
-15             -10                  -5                   1

Ala Lys His Lys Gln Arg Lys Arg Leu Lys Ser Ser Cys Lys Arg His
             5                  10                  15

Pro Leu Tyr Val Asp Phe Ser Asp Val Gly Trp Asn Asp Trp Ile Val
            20                  25                  30

Ala Pro Pro Gly Tyr His Ala Phe Tyr Cys His Gly Glu Cys Pro Phe
        35                  40                  45

Pro Leu Ala Asp His Leu Asn Ser Thr Asn His Ala Ile Val Gln Thr
 50              55                  60                  65

Leu Val Asn Ser Val Asn Ser Lys Ile Pro Lys Ala Cys Cys Val Pro
             70                  75                  80

Thr Glu Leu Ser Ala Ile Ser Met Leu Tyr Leu Asp Glu Asn Glu Lys
                 85                  90                  95

Val Val Leu Lys Asn Tyr Gln Asp Met Val Val Glu Gly Cys Gly Cys
            100                 105                 110

Arg (2) INFORMATION FOR SEQ ID NO:3:

(i) SEQUENCE CHARACTERISTICS:
        (A) LENGTH: 1607 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO
```

-continued (vi) ORIGINAL SOURCE:
    (A) ORGANISM: Homo Sapiens
    (G) CELL TYPE: Osteosarcoma Cell Line
    (H) CELL LINE: U-2OS (vii) IMMEDIATE SOURCE:
    (A) LIBRARY: U2OS cDNA in Lambda GT10
    (B) CLONE: Lambda U2OS-39

(viii) POSITION IN GENOME:
    (C) UNITS: bp (ix) FEATURE:
    (A) NAME/KEY: CDS
    (B) LOCATION: 356..1546

(ix) FEATURE:
    (A) NAME/KEY: mat_peptide
    (B) LOCATION: 1202..1543

(ix) FEATURE:
    (A) NAME/KEY: mRNA
    (B) LOCATION: 14..1607

(ix) FEATURE:
    (A) NAME/KEY: sig_peptide
    (B) LOCATION: 356..424

(xi) SEQUENCE DESCRIPTION: SEQ ID NO:3:

```
GTCGACTCTA GAGTGTGTGT CAGCACTTGG CTGGGGACTT CTTGAACTTG CAGGGAGAAT       60

AACTTGCGCA CCCCACTTTG CGCCGGTGCC TTTGCCCCAG CGGAGCCTGC TTCGCCATCT      120

CCGAGCCCCA CCGCCCCTCC ACTCCTCGGC CTTGCCCGAC ACTGAGACGC TGTTCCCAGC      180

GTGAAAAGAG AGACTGCGCG GCCGGCACCC GGGAGAAGGA GGAGGCAAAG AAAAGGAACG      240

GACATTCGGT CCTTGCGCCA GGTCCTTTGA CCAGAGTTTT TCCATGTGGA CGCTCTTTCA      300

ATGGACGTGT CCCCGCGTGC TTCTTAGACG GACTGCGGTC TCCTAAAGGT CGACC ATG       358
                                                               Met
                                                               -282

GTG GCC GGG ACC CGC TGT CTT CTA GCG TTG CTG CTT CCC CAG GTC CTC        406
Val Ala Gly Thr Arg Cys Leu Leu Ala Leu Leu Leu Pro Gln Val Leu
    -280                -275                -270

CTG GGC GGC GCG GCT GGC CTC GTT CCG GAG CTG GGC CGC AGG AAG TTC        454
Leu Gly Gly Ala Ala Gly Leu Val Pro Glu Leu Gly Arg Arg Lys Phe
-265                -260                -255                -250

GCG GCG GCG TCG TCG GGC CGC CCC TCA TCC CAG CCC TCT GAC GAG GTC        502
Ala Ala Ala Ser Ser Gly Arg Pro Ser Ser Gln Pro Ser Asp Glu Val
                -245                -240                -235

CTG AGC GAG TTC GAG TTG CGG CTG CTC AGC ATG TTC GGC CTG AAA CAG        550
Leu Ser Glu Phe Glu Leu Arg Leu Leu Ser Met Phe Gly Leu Lys Gln
            -230                -225                -220

AGA CCC ACC CCC AGC AGG GAC GCC GTG GTG CCC CCC TAC ATG CTA GAC        598
Arg Pro Thr Pro Ser Arg Asp Ala Val Val Pro Pro Tyr Met Leu Asp
        -215                -210                -205

CTG TAT CGC AGG CAC TCA GGT CAG CCG GGC TCA CCC GCC CCA GAC CAC        646
Leu Tyr Arg Arg His Ser Gly Gln Pro Gly Ser Pro Ala Pro Asp His
    -200                -195                -190

CGG TTG GAG AGG GCA GCC AGC CGA GCC AAC ACT GTG CGC AGC TTC CAC        694
Arg Leu Glu Arg Ala Ala Ser Arg Ala Asn Thr Val Arg Ser Phe His
-185                -180                -175                -170

CAT GAA GAA TCT TTG GAA GAA CTA CCA GAA ACG AGT GGG AAA ACA ACC        742
His Glu Glu Ser Leu Glu Glu Leu Pro Glu Thr Ser Gly Lys Thr Thr
                -165                -160                -155

CGG AGA TTC TTC TTT AAT TTA AGT TCT ATC CCC ACG GAG GAG TTT ATC        790
Arg Arg Phe Phe Phe Asn Leu Ser Ser Ile Pro Thr Glu Glu Phe Ile
            -150                -145                -140
```

```
ACC TCA GCA GAG CTT CAG GTT TTC CGA GAA CAG ATG CAA GAT GCT TTA      838
Thr Ser Ala Glu Leu Gln Val Phe Arg Glu Gln Met Gln Asp Ala Leu
        -135             -130             -125

GGA AAC AAT AGC AGT TTC CAT CAC CGA ATT AAT ATT TAT GAA ATC ATA      886
Gly Asn Asn Ser Ser Phe His His Arg Ile Asn Ile Tyr Glu Ile Ile
        -120             -115             -110

AAA CCT GCA ACA GCC AAC TCG AAA TTC CCC GTG ACC AGA CTT TTG GAC      934
Lys Pro Ala Thr Ala Asn Ser Lys Phe Pro Val Thr Arg Leu Leu Asp
-105             -100             -95                       -90

ACC AGG TTG GTG AAT CAG AAT GCA AGC AGG TGG GAA AGT TTT GAT GTC      982
Thr Arg Leu Val Asn Gln Asn Ala Ser Arg Trp Glu Ser Phe Asp Val
                -85              -80              -75

ACC CCC GCT GTG ATG CGG TGG ACT GCA CAG GGA CAC GCC AAC CAT GGA     1030
Thr Pro Ala Val Met Arg Trp Thr Ala Gln Gly His Ala Asn His Gly
            -70              -65              -60

TTC GTG GTG GAA GTG GCC CAC TTG GAG GAG AAA CAA GGT GTC TCC AAG     1078
Phe Val Val Glu Val Ala His Leu Glu Glu Lys Gln Gly Val Ser Lys
        -55              -50              -45

AGA CAT GTT AGG ATA AGC AGG TCT TTG CAC CAA GAT GAA CAC AGC TGG     1126
Arg His Val Arg Ile Ser Arg Ser Leu His Gln Asp Glu His Ser Trp
    -40              -35              -30

TCA CAG ATA AGG CCA TTG CTA GTA ACT TTT GGC CAT GAT GGA AAA GGG     1174
Ser Gln Ile Arg Pro Leu Leu Val Thr Phe Gly His Asp Gly Lys Gly
-25              -20              -15              -10

CAT CCT CTC CAC AAA AGA GAA AAA CGT CAA GCC AAA CAC AAA CAG CGG     1222
His Pro Leu His Lys Arg Glu Lys Arg Gln Ala Lys His Lys Gln Arg
                -5                1                5

AAA CGC CTT AAG TCC AGC TGT AAG AGA CAC CCT TTG TAC GTG GAC TTC     1270
Lys Arg Leu Lys Ser Ser Cys Lys Arg His Pro Leu Tyr Val Asp Phe
        10               15               20

AGT GAC GTG GGG TGG AAT GAC TGG ATT GTG GCT CCC CCG GGG TAT CAC     1318
Ser Asp Val Gly Trp Asn Asp Trp Ile Val Ala Pro Pro Gly Tyr His
        25               30               35

GCC TTT TAC TGC CAC GGA GAA TGC CCT TTT CCT CTG GCT GAT CAT CTG     1366
Ala Phe Tyr Cys His Gly Glu Cys Pro Phe Pro Leu Ala Asp His Leu
40               45               50               55

AAC TCC ACT AAT CAT GCC ATT GTT CAG ACG TTG GTC AAC TCT GTT AAC     1414
Asn Ser Thr Asn His Ala Ile Val Gln Thr Leu Val Asn Ser Val Asn
                 60               65               70

TCT AAG ATT CCT AAG GCA TGC TGT GTC CCG ACA GAA CTC AGT GCT ATC     1462
Ser Lys Ile Pro Lys Ala Cys Cys Val Pro Thr Glu Leu Ser Ala Ile
        75               80               85

TCG ATG CTG TAC CTT GAC GAG AAT GAA AAG GTT GTA TTA AAG AAC TAT     1510
Ser Met Leu Tyr Leu Asp Glu Asn Glu Lys Val Val Leu Lys Asn Tyr
        90               95              100

CAG GAC ATG GTT GTG GAG GGT TGT GGG TGT CGC TAGTACAGCA AAATTAAATA   1563
Gln Asp Met Val Val Glu Gly Cys Gly Cys Arg
105             110             115

CATAAATATA TATATATATA TATATTTTAG AAAAAAGAAA AAAA                    1607

(2) INFORMATION FOR SEQ ID NO:4:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:4:
```

-continued

```
Met Val Ala Gly Thr Arg Cys Leu Leu Ala Leu Leu Pro Gln Val
-282     -280              -275              -270

Leu Leu Gly Gly Ala Ala Gly Leu Val Pro Glu Leu Gly Arg Arg Lys
        -265              -260              -255

Phe Ala Ala Ala Ser Ser Gly Arg Pro Ser Ser Gln Pro Ser Asp Glu
-250             -245              -240              -235

Val Leu Ser Glu Phe Glu Leu Arg Leu Leu Ser Met Phe Gly Leu Lys
            -230              -225              -220

Gln Arg Pro Thr Pro Ser Arg Asp Ala Val Pro Pro Tyr Met Leu
            -215              -210              -205

Asp Leu Tyr Arg Arg His Ser Gly Gln Pro Gly Ser Pro Ala Pro Asp
        -200              -195              -190

His Arg Leu Glu Arg Ala Ala Ser Arg Ala Asn Thr Val Arg Ser Phe
-185             -180              -175

His His Glu Glu Ser Leu Glu Glu Leu Pro Glu Thr Ser Gly Lys Thr
-170             -165              -160              -155

Thr Arg Arg Phe Phe Phe Asn Leu Ser Ser Ile Pro Thr Glu Glu Phe
                -150              -145              -140

Ile Thr Ser Ala Glu Leu Gln Val Phe Arg Gln Met Gln Asp Ala
                -135              -130              -125

Leu Gly Asn Asn Ser Ser Phe His His Arg Ile Asn Ile Tyr Glu Ile
            -120              -115              -110

Ile Lys Pro Ala Thr Ala Asn Ser Lys Phe Pro Val Thr Arg Leu Leu
    -105              -100              -95

Asp Thr Arg Leu Val Asn Gln Asn Ala Ser Arg Trp Glu Ser Phe Asp
-90              -85               -80                    -75

Val Thr Pro Ala Val Met Arg Trp Thr Ala Gln Gly His Ala Asn His
                -70               -65                    -60

Gly Phe Val Val Glu Val Ala His Leu Glu Glu Lys Gln Gly Val Ser
                -55               -50                    -45

Lys Arg His Val Arg Ile Ser Arg Ser Leu His Gln Asp Glu His Ser
        -40               -35                    -30

Trp Ser Gln Ile Arg Pro Leu Leu Val Thr Phe Gly His Asp Gly Lys
    -25               -20                    -15

Gly His Pro Leu His Lys Arg Glu Lys Arg Gln Ala Lys His Lys Gln
-10              -5                1                     5

Arg Lys Arg Leu Lys Ser Ser Cys Lys Arg His Pro Leu Tyr Val Asp
                10                15                    20

Phe Ser Asp Val Gly Trp Asn Asp Trp Ile Val Ala Pro Pro Gly Tyr
            25                30                    35

His Ala Phe Tyr Cys His Gly Glu Cys Pro Phe Pro Leu Ala Asp His
    40                45                    50

Leu Asn Ser Thr Asn His Ala Ile Val Gln Thr Leu Val Asn Ser Val
55                60                65                    70

Asn Ser Lys Ile Pro Lys Ala Cys Cys Val Pro Thr Glu Leu Ser Ala
            75                80                    85

Ile Ser Met Leu Tyr Leu Asp Glu Asn Glu Lys Val Val Leu Lys Asn
            90                95                    100

Tyr Gln Asp Met Val Val Glu Gly Cys Gly Cys Arg
            105               110
```

(2) INFORMATION FOR SEQ ID NO:5:

(i) SEQUENCE CHARACTERISTICS:

(A) LENGTH: 1954 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo Sapiens (vii) IMMEDIATE SOURCE:
        (A) LIBRARY: U2OS cDNA in Lambda gt10
        (B) CLONE: Lambda U2OS-3

(viii) POSITION IN GENOME:
        (C) UNITS: bp (ix) FEATURE:
        (A) NAME/KEY: CDS
        (B) LOCATION: 403..1629

(ix) FEATURE:
        (A) NAME/KEY: mat_peptide
        (B) LOCATION: 1279..1629

(ix) FEATURE:
        (A) NAME/KEY: mRNA
        (B) LOCATION: 9..1934

(xi) SEQUENCE DESCRIPTION: SEQ ID NO:5:

```
CTCTAGAGGG CAGAGGAGGA GGGAGGGAGG GAAGGAGCGC GGAGCCCGGC CCGGAAGCTA      60

GGTGAGTGTG GCATCCGAGC TGAGGGACGC GAGCCTGAGA CGCCGCTGCT GCTCCGGCTG     120

AGTATCTAGC TTGTCTCCCC GATGGGATTC CCGTCCAAGC TATCTCGAGC CTGCAGCGCC     180

ACAGTCCCCG GCCCTCGCCC AGGTTCACTG CAACCGTTCA GAGGTCCCCA GGAGCTGCTG     240

CTGGCGAGCC CGCTACTGCA GGGACCTATG GAGCCATTCC GTAGTGCCAT CCCGAGCAAC     300

GCACTGCTGC AGCTTCCCTG AGCCTTTCCA GCAAGTTTGT TCAAGATTGG CTGTCAAGAA     360

TCATGGACTG TTATTATATG CCTTGTTTTC TGTCAAGACA CC ATG ATT CCT GGT       414
                                              Met Ile Pro Gly
                                              -292        -290

AAC CGA ATG CTG ATG GTC GTT TTA TTA TGC CAA GTC CTG CTA GGA GGC       462
Asn Arg Met Leu Met Val Val Leu Leu Cys Gln Val Leu Leu Gly Gly
        -285            -280            -275

GCG AGC CAT GCT AGT TTG ATA CCT GAG ACG GGG AAG AAA AAA GTC GCC       510
Ala Ser His Ala Ser Leu Ile Pro Glu Thr Gly Lys Lys Lys Val Ala
    -270            -265            -260

GAG ATT CAG GGC CAC GCG GGA GGA CGC CGC TCA GGG CAG AGC CAT GAG       558
Glu Ile Gln Gly His Ala Gly Gly Arg Arg Ser Gly Gln Ser His Glu
    -255            -250            -245

CTC CTG CGG GAC TTC GAG GCG ACA CTT CTG CAG ATG TTT GGG CTG CGC       606
Leu Leu Arg Asp Phe Glu Ala Thr Leu Leu Gln Met Phe Gly Leu Arg
-240            -235            -230            -225

CGC CGC CCG CAG CCT AGC AAG AGT GCC GTC ATT CCG GAC TAC ATG CGG       654
Arg Arg Pro Gln Pro Ser Lys Ser Ala Val Ile Pro Asp Tyr Met Arg
            -220            -215            -210

GAT CTT TAC CGG CTT CAG TCT GGG GAG GAG GAG GAA GAG CAG ATC CAC       702
Asp Leu Tyr Arg Leu Gln Ser Gly Glu Glu Glu Glu Glu Gln Ile His
            -205            -200            -195

AGC ACT GGT CTT GAG TAT CCT GAG CGC CCG GCC AGC CGG GCC AAC ACC       750
Ser Thr Gly Leu Glu Tyr Pro Glu Arg Pro Ala Ser Arg Ala Asn Thr
        -190            -185            -180
```

-continued

| | |
|---|---|
| GTG AGG AGC TTC CAC CAC GAA GAA CAT CTG GAG AAC ATC CCA GGG ACC<br>Val Arg Ser Phe His His Glu Glu His Leu Glu Asn Ile Pro Gly Thr<br>    -175                -170                  -165 | 798 |
| AGT GAA AAC TCT GCT TTT CGT TTC CTC TTT AAC CTC AGC AGC ATC CCT<br>Ser Glu Asn Ser Ala Phe Arg Phe Leu Phe Asn Leu Ser Ser Ile Pro<br>-160                -155                -150                  -145 | 846 |
| GAG AAC GAG GTG ATC TCC TCT GCA GAG CTT CGG CTC TTC CGG GAG CAG<br>Glu Asn Glu Val Ile Ser Ser Ala Glu Leu Arg Leu Phe Arg Glu Gln<br>                  -140                -135                -130 | 894 |
| GTG GAC CAG GGC CCT GAT TGG GAA AGG GGC TTC CAC CGT ATA AAC ATT<br>Val Asp Gln Gly Pro Asp Trp Glu Arg Gly Phe His Arg Ile Asn Ile<br>            -125                -120                -115 | 942 |
| TAT GAG GTT ATG AAG CCC CCA GCA GAA GTG GTG CCT GGG CAC CTC ATC<br>Tyr Glu Val Met Lys Pro Pro Ala Glu Val Val Pro Gly His Leu Ile<br>        -110                -105                -100 | 990 |
| ACA CGA CTA CTG GAC ACG AGA CTG GTC CAC CAC AAT GTG ACA CGG TGG<br>Thr Arg Leu Leu Asp Thr Arg Leu Val His His Asn Val Thr Arg Trp<br>    -95                -90                -85 | 1038 |
| GAA ACT TTT GAT GTG AGC CCT GCG GTC CTT CGC TGG ACC CGG GAG AAG<br>Glu Thr Phe Asp Val Ser Pro Ala Val Leu Arg Trp Thr Arg Glu Lys<br>-80                 -75                -70                 -65 | 1086 |
| CAG CCA AAC TAT GGG CTA GCC ATT GAG GTG ACT CAC CTC CAT CAG ACT<br>Gln Pro Asn Tyr Gly Leu Ala Ile Glu Val Thr His Leu His Gln Thr<br>            -60                -55                -50 | 1134 |
| CGG ACC CAC CAG GGC CAG CAT GTC AGG ATT AGC CGA TCG TTA CCT CAA<br>Arg Thr His Gln Gly Gln His Val Arg Ile Ser Arg Ser Leu Pro Gln<br>            -45                -40                -35 | 1182 |
| GGG AGT GGG AAT TGG GCC CAG CTC CGG CCC CTC CTG GTC ACC TTT GGC<br>Gly Ser Gly Asn Trp Ala Gln Leu Arg Pro Leu Leu Val Thr Phe Gly<br>        -30                -25                -20 | 1230 |
| CAT GAT GGC CGG GGC CAT GCC TTG ACC CGA CGC CGG AGG GCC AAG CGT<br>His Asp Gly Arg Gly His Ala Leu Thr Arg Arg Arg Arg Ala Lys Arg<br>    -15                -10                 -5 | 1278 |
| AGC CCT AAG CAT CAC TCA CAG CGG GCC AGG AAG AAG AAT AAG AAC TGC<br>Ser Pro Lys His His Ser Gln Arg Ala Arg Lys Lys Asn Lys Asn Cys<br>1                  5                   10                  15 | 1326 |
| CGG CGC CAC TCG CTC TAT GTG GAC TTC AGC GAT GTG GGC TGG AAT GAC<br>Arg Arg His Ser Leu Tyr Val Asp Phe Ser Asp Val Gly Trp Asn Asp<br>         20                 25                 30 | 1374 |
| TGG ATT GTG GCC CCA CCA GGC TAC CAG GCC TTC TAC TGC CAT GGG GAC<br>Trp Ile Val Ala Pro Pro Gly Tyr Gln Ala Phe Tyr Cys His Gly Asp<br>     35                 40                 45 | 1422 |
| TGC CCC TTT CCA CTG GCT GAC CAC CTC AAC TCA ACC AAC CAT GCC ATT<br>Cys Pro Phe Pro Leu Ala Asp His Leu Asn Ser Thr Asn His Ala Ile<br>50                   55                  60 | 1470 |
| GTG CAG ACC CTG GTC AAT TCT GTC AAT TCC AGT ATC CCC AAA GCC TGT<br>Val Gln Thr Leu Val Asn Ser Val Asn Ser Ser Ile Pro Lys Ala Cys<br>65                   70                  75                 80 | 1518 |
| TGT GTG CCC ACT GAA CTG AGT GCC ATC TCC ATG CTG TAC CTG GAT GAG<br>Cys Val Pro Thr Glu Leu Ser Ala Ile Ser Met Leu Tyr Leu Asp Glu<br>            85                 90                 95 | 1566 |
| TAT GAT AAG GTG GTA CTG AAA AAT TAT CAG GAG ATG GTA GTA GAG GGA<br>Tyr Asp Lys Val Val Leu Lys Asn Tyr Gln Glu Met Val Val Glu Gly<br>          100                105                110 | 1614 |
| TGT GGG TGC CGC TGAGATCAGG CAGTCCTTGA GGATAGACAG ATATACACAC<br>Cys Gly Cys Arg<br>          115 | 1666 |
| CACACACACA CACCACATAC ACCACACACA CACGTTCCCA TCCACTCACC CACACACTAC | 1726 |
| ACAGACTGCT TCCTTATAGC TGGACTTTTA TTTAAAAAAA AAAAAAAAAA AATGGAAAAA | 1786 |

```
ATCCCTAAAC ATTCACCTTG ACCTTATTTA TGACTTTACG TGCAAATGTT TTGACCATAT    1846

TGATCATATA TTTTGACAAA ATATATTTAT AACTACGTAT TAAAAGAAAA AAATAAAATG    1906

AGTCATTATT TTAAAAAAAA AAAAAAAACT CTAGAGTCGA CGGAATTC                 1954
```

(2) INFORMATION FOR SEQ ID NO:6:

(i) SEQUENCE CHARACTERISTICS:
        (A) LENGTH: 408 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ile Pro Gly Asn Arg Met Leu Met Val Val Leu Leu Cys Gln Val
-292     -290          -285              -280

Leu Leu Gly Gly Ala Ser His Ala Ser Leu Ile Pro Glu Thr Gly Lys
        -275          -270              -265

Lys Lys Val Ala Glu Ile Gln Gly His Ala Gly Gly Arg Arg Ser Gly
-260          -255              -250              -245

Gln Ser His Glu Leu Leu Arg Asp Phe Glu Ala Thr Leu Leu Gln Met
             -240              -235              -230

Phe Gly Leu Arg Arg Arg Pro Gln Pro Ser Lys Ser Ala Val Ile Pro
        -225              -220              -215

Asp Tyr Met Arg Asp Leu Tyr Arg Leu Gln Ser Gly Glu Glu Glu Glu
        -210              -205              -200

Glu Gln Ile His Ser Thr Gly Leu Glu Tyr Pro Glu Arg Pro Ala Ser
    -195              -190              -185

Arg Ala Asn Thr Val Arg Ser Phe His His Glu Glu His Leu Glu Asn
-180              -175              -170              -165

Ile Pro Gly Thr Ser Glu Asn Ser Ala Phe Arg Phe Leu Phe Asn Leu
             -160              -155              -150

Ser Ser Ile Pro Glu Asn Glu Val Ile Ser Ser Ala Glu Leu Arg Leu
        -145              -140              -135

Phe Arg Glu Gln Val Asp Gln Gly Pro Asp Trp Glu Arg Gly Phe His
        -130              -125              -120

Arg Ile Asn Ile Tyr Glu Val Met Lys Pro Pro Ala Glu Val Val Pro
-115              -110              -105

Gly His Leu Ile Thr Arg Leu Leu Asp Thr Arg Leu Val His His Asn
-100          -95               -90               -85

Val Thr Arg Trp Glu Thr Phe Asp Val Ser Pro Ala Val Leu Arg Trp
             -80               -75               -70

Thr Arg Glu Lys Gln Pro Asn Tyr Gly Leu Ala Ile Glu Val Thr His
        -65               -60               -55

Leu His Gln Thr Arg Thr His Gln Gly Gln His Val Arg Ile Ser Arg
        -50               -45               -40

Ser Leu Pro Gln Gly Ser Gly Asn Trp Ala Gln Leu Arg Pro Leu Leu
    -35               -30               -25

Val Thr Phe Gly His Asp Gly Arg Gly His Ala Leu Thr Arg Arg Arg
-20              -15               -10                -5

Arg Ala Lys Arg Ser Pro Lys His His Ser Gln Arg Ala Arg Lys Lys
              1                 5                  10

Asn Lys Asn Cys Arg Arg His Ser Leu Tyr Val Asp Phe Ser Asp Val
         15                20                25
```

-continued

| | | | | | | | | | | | |
|---|---|---|---|---|---|---|---|---|---|---|---|
|Gly|Trp|Asn|Asp|Trp|Ile|Val|Ala|Pro|Pro|Gly|Tyr|Gln|Ala|Phe|Tyr|
| |30| | | |35| | | |40| | | | | | |
|Cys|His|Gly|Asp|Cys|Pro|Phe|Pro|Leu|Ala|Asp|His|Leu|Asn|Ser|Thr|
|45| | | |50| | | |55| | | | | | |60|
|Asn|His|Ala|Ile|Val|Gln|Thr|Leu|Val|Asn|Ser|Val|Asn|Ser|Ser|Ile|
| | | | |65| | | |70| | | | |75| | |
|Pro|Lys|Ala|Cys|Cys|Val|Pro|Thr|Glu|Leu|Ser|Ala|Ile|Ser|Met|Leu|
| | | |80| | | | |85| | | | |90| | |
|Tyr|Leu|Asp|Glu|Tyr|Asp|Lys|Val|Val|Leu|Lys|Asn|Tyr|Gln|Glu|Met|
| | |95| | | |100| | | | |105| | | | |
|Val|Val|Glu|Gly|Cys|Gly|Cys|Arg|
| |110| | | |115| | |